(12) United States Patent
Kim et al.

(10) Patent No.: US 12,408,864 B2
(45) Date of Patent: Sep. 9, 2025

(54) ARTIFICIAL NEURAL NETWORK-BASED NUCLEAR MAGNETIC RESONANCE AND MAGNETIC RESONANCE SPECTROSCOPY DATA PROCESSING METHOD AND APPARATUS THEREOF

(71) Applicant: SEOUL NATIONAL UNIVERSITY R&DB FOUNDATION, Seoul (KR)

(72) Inventors: Hyeonjin Kim, Seoul (KR); Hyeong Hun Lee, Gyeonggi-do (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 429 days.

(21) Appl. No.: 17/430,461

(22) PCT Filed: Apr. 7, 2020

(86) PCT No.: PCT/KR2020/004655
§ 371 (c)(1),
(2) Date: Aug. 12, 2021

(87) PCT Pub. No.: WO2020/209566
PCT Pub. Date: Oct. 15, 2020

(65) Prior Publication Data
US 2022/0117552 A1    Apr. 21, 2022

(30) Foreign Application Priority Data

Apr. 8, 2019   (KR) .................. 10-2019-0041059
Apr. 6, 2020   (KR) .................. 10-2020-0041497

(51) Int. Cl.
*A61B 5/00*   (2006.01)
*A61B 5/055*   (2006.01)

(52) U.S. Cl.
CPC ............ *A61B 5/4866* (2013.01); *A61B 5/055* (2013.01); *A61B 5/7264* (2013.01)

(58) Field of Classification Search
CPC ...... A61B 5/4866; A61B 5/055; A61B 5/7264
See application file for complete search history.

(56) References Cited

U.S. PATENT DOCUMENTS 5,887,588 A * 3/1999 Usenius ................. A61B 5/055
706/924
10,198,799 B2   2/2019 Park et al.
(Continued)

FOREIGN PATENT DOCUMENTS

JP   5873280 A    3/2016
JP   2017225688 A   12/2017
(Continued)

OTHER PUBLICATIONS

Steinberg et al., Improved Initial Value Estimation for Short Echo Time Magnetic Resonance Spectroscopy Spectral Analysis Using Short T2 Signal Attenuation, 2012, Magnetic Resonance in Medicine, 67:1195-1202 (Year: 2012).*

(Continued)

*Primary Examiner* — Keith M Raymond
*Assistant Examiner* — Andrew W Begeman
(74) *Attorney, Agent, or Firm* — Kilpatrick Townsend & Stockton LLP

(57) ABSTRACT

An apparatus for processing nuclear magnetic resonance and magnetic resonance spectroscopy data may include: a data input unit configured to receive input data from a magnetic resonator, define incomplete data from the input data based on a sampling time, and classify, based on a preset criterion, remaining data of the input data except the incomplete data as ground truth data satisfying the preset criterion or bad data not satisfying the preset criterion; a data recovery unit configured to obtain recovered data by recovering the incomplete data and the bad data which are received from the data input unit; and a disease diagnosis unit configured to generate metabolite quantification data based on a (Continued)

metabolite concentration range by using the ground truth data received from the data input unit and the recovered data received from the data recovery unit.

8 Claims, 39 Drawing Sheets

(56) References Cited

U.S. PATENT DOCUMENTS

| | | | |
|---|---|---|---|
| 2005/0251025 A1* | 11/2005 | Hancu | G01R 33/465 600/431 |
| 2018/0293762 A1 | 10/2018 | Fu et al. | |
| 2019/0206527 A1* | 7/2019 | Boehm | A61B 5/055 |
| 2020/0258199 A1 | 8/2020 | Shirai et al. | |
| 2021/0027891 A1* | 1/2021 | Rajput | G16H 70/40 |
| 2021/0190891 A1* | 6/2021 | Mandal | G01R 33/5608 |

FOREIGN PATENT DOCUMENTS

| | | |
|---|---|---|
| JP | 2019-042444 A | 3/2019 |
| KR | 10-1659578 B1 | 9/2016 |

OTHER PUBLICATIONS

Hui et al., "Mri Reconstruction From Truncated Data Using a Complex Domain Backpropagation Neural Network" 1995, IEEE, 0-7803-2553-2/95/$4.00, p. 513-516 (Year: 1995).*

Alkan et al., "Magnetic Resonance Contrast Prediction Using Deep Learning," Class Material (cs231n) Stanford University (2017), 7 pages.

Behar et al., "Characterization of Macromolecule Resonances in the $^1$H NMR Spectrum of Rat Brain," Magnetic Resonance in Medicine (1993) 30; 38-44.

Bhogal et al., "1H-MRS processing parameters affect metabolite quantification: The urgent need for uniform and transparent standardization," Wiley NMR in Biomedicine, DOI: 10.1002/nbm.3804 (2017),9 pages.

Birch et al., "Influence of Macromolecule Baseline on $^1$H MR Spectroscopic Imaging Reproducibility," Magnetic Resonance in Medicine 00:00-00 (2016) 10 pages.

Cobbold, et al., "Hepatic lipid profiling in chronic hepatitis C: An in vitro and in vivo proton magnetic resonance spectroscopy study," Journal of Hepatology 2010 vol. 52(1); 16-24.

Heo et al., "On the Utility of Short Echo Time (TE) Single Voxel 1H-MRS in Non-Invasive Detection of 2-Hydroxyglutarate (2HG): Challenges and Potential Improvement Illustrated with Animal Models Using MRUI and LCModel," PLoS One DOI: 10.12371/journal.pone. 0147794 Jan. 28, 2016, 18 pages.

International Search Report and Written Opinion for PCT/KR2020/004655 dated Jul. 13, 2020, all pages.

Kreis, Roland, "The Trouble With Quality Filtering Based on Relative Cramer-Rao Lower Bounds," Magnetic Resonance in Medicine 75:15-18 (2016), 4 pages.

Kyathanahally et al., "Deep Learning Approaches for Detection and Removal of Ghosting Artifacts in MR Spectroscopy," Magnetic Resonance in Medicine 80:851-863 (2018).

LeCun et al., "Deep Learning," Nature, vol. 521, May 28, 2015, doi: 10.1038/nature14539, 10 pages.

Litjens, et al., "A Survey on Deep Learning in Medical Image Analysis," Diagnostic Image Analysis Group, Radboud University Medical Center, Nijmegen, The Netherlands, arXiv:1702.05747v2 [cs.CV] Jun. 4, 2017, 38 pages.

Notification of Reason for Refusal for Korean AppIn No. 10-2020-0041497 dispatched on Jun. 24, 2021, all pages.

Nguyen et al., "Cross-Domain Synthesis of Medical Images Using Efficient Location-Sensitive Deep Network," MICCAI 2015, LNCS, vol. 9349, pp. 677-684, Springer, Heidelberg (2015), 8 pages.

Opstad et al., "Toward Accurate Quantification of Metabolies, Lipids, and Macromolecules in HRMAS Spectra of Human Brain Tumor Biopsies Using LCModel," Magnetic Resonance in Medicine 60:1237-1242 (2008).

Pfeuffer et al., "Toward an in Vivo Neurochemical Profile: Quantification of 18 Metabolites in Short-Echo-Time $^1$H NMR Spectra of the Rat Brain," Journal of Magnetic Resonance 141, 104-120 (1999) jmre.1999.1895, http://www.idealibrary.com.

Provencher, Stephen W., "Estimation of Metabolite Concentrations from Localized in Vivo Proton NMR Spectra," Magnetic Resonance in Medicine 1993;30; 672-679.

Ratiney, et al., "Time-domain quantitation of $^1$H short echo-time signals: background accommodation," MAGMA (2004) 16: 284-296 DOI 10.1007/s10334-004-0037-9, 13 pages.

Seeger, et al., "Parameterized Evaluation of Macromolecules and Lipids in Proton MR Spectroscopy of Brain Diseases," Magnetic Resonance in Medicine 49:19-28 (2003).

Sevetlidis et al., "Whole Image Synthesis Using a Deep Encoder-Decoder Network," International Workshop on Simulation and Synthesis in Medical Imaging 2016, pp. 127-137 DOI: 10.1007/978-3-319-46630-9_13.

* cited by examiner

FIG. 16
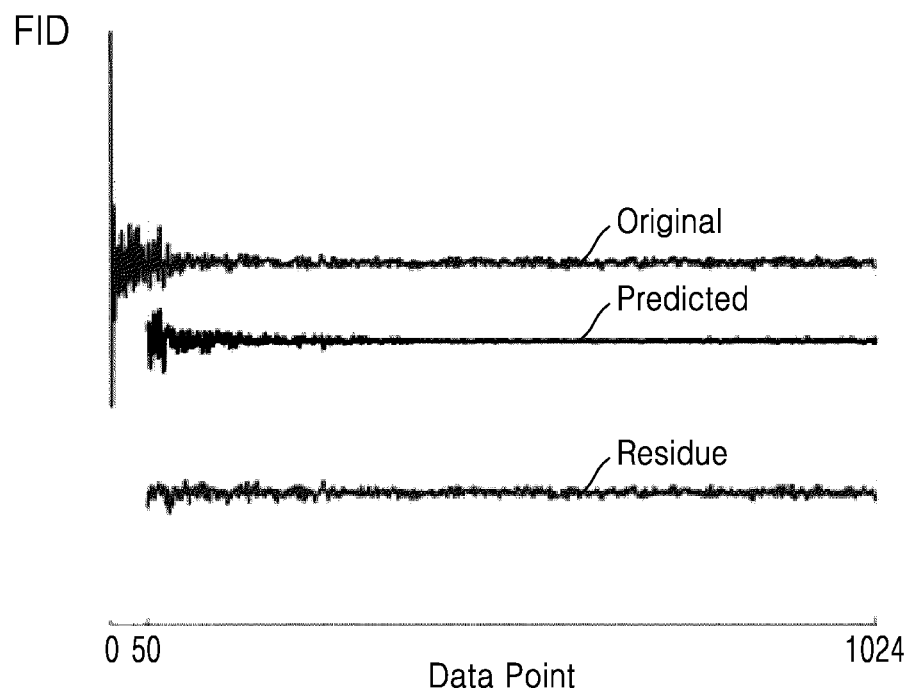
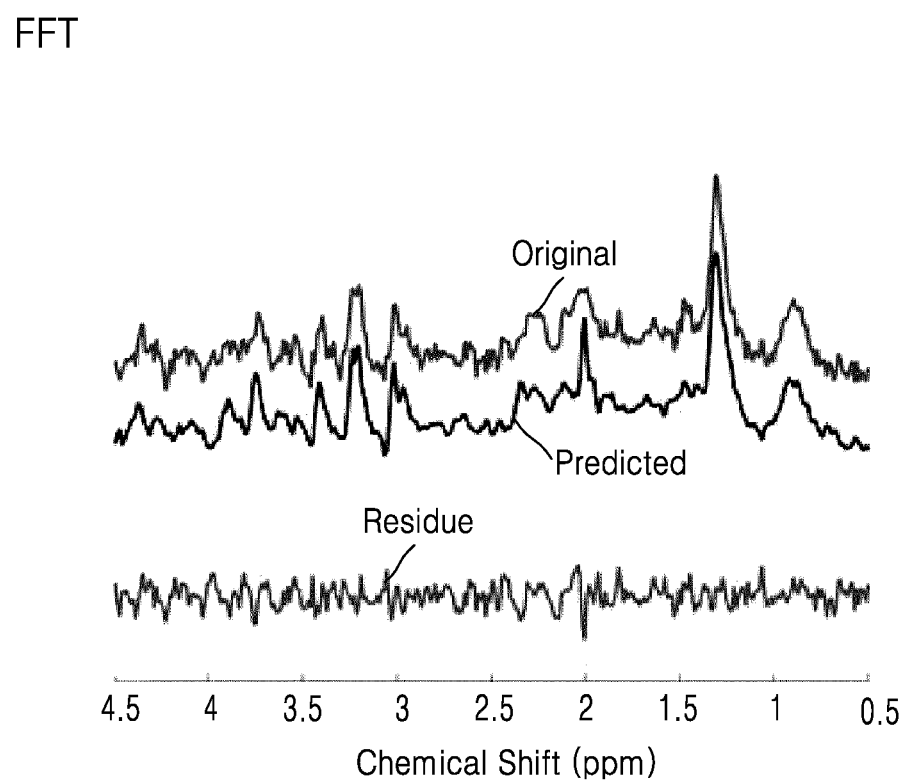

FIG. 17
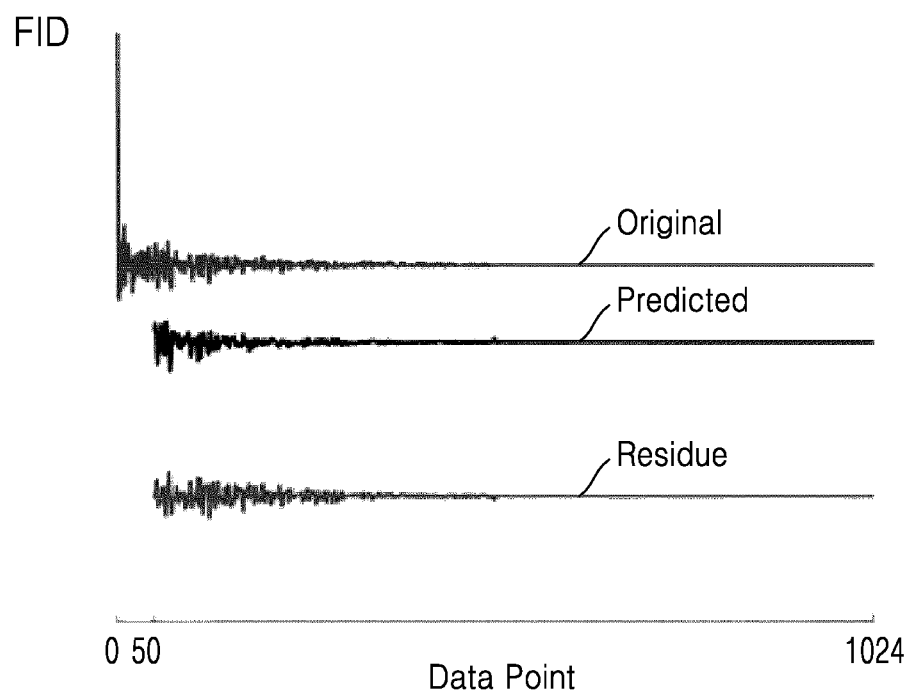
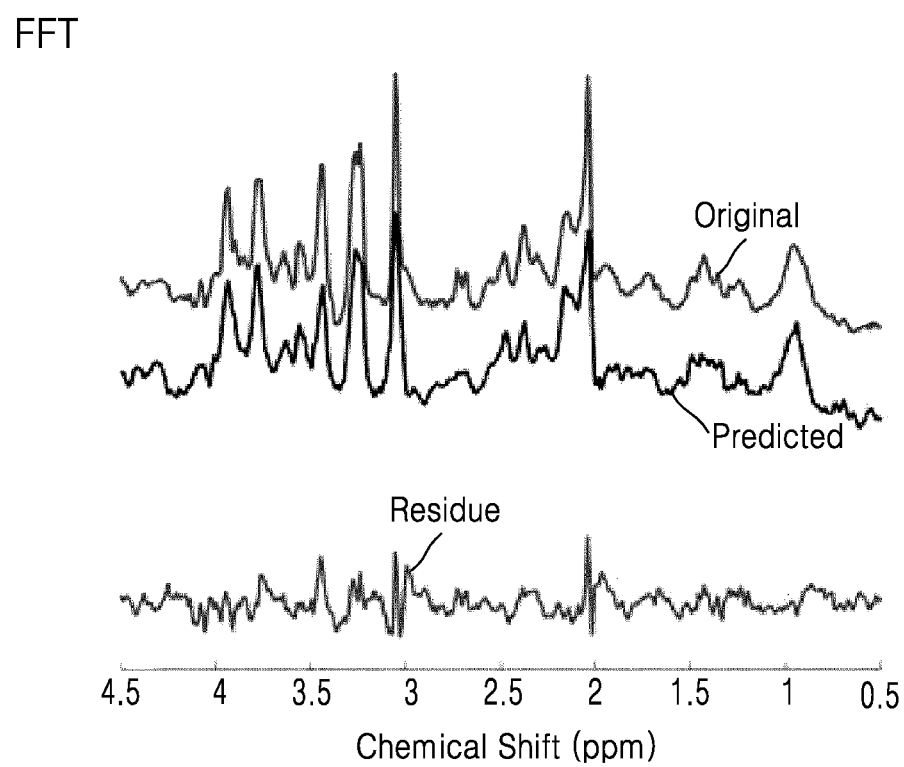

FIG. 21

Mean absolute error (%)

| Metabolite | Ala | Asp | GABA | Glc | Glu | Gln | GSH | GPC | Lac | mI | NAA | NAAG | PC | PE | Tau |
|---|---|---|---|---|---|---|---|---|---|---|---|---|---|---|---|
| Target | 21.77 | 9.90 | 9.55 | 10.29 | 3.03 | 4.58 | 6.00 | 22.01 | 8.50 | 2.70 | 2.65 | 23.90 | 13.58 | 10.29 | 2.84 |
| Cr+PCr 3.0ppm | 2.21 | 1.86 | 2.20 | 1.96 | 2.38 | 2.29 | 1.88 | 2.95 | 2.10 | 2.20 | 2.19 | 2.22 | 2.69 | 2.08 | 2.15 |
| Cr+PCr 3.9ppm | 2.36 | 1.99 | 2.27 | 1.80 | 2.40 | 2.32 | 2.12 | 2.72 | 2.10 | 2.08 | 2.33 | 2.33 | 2.20 | 2.32 | 2.26 |

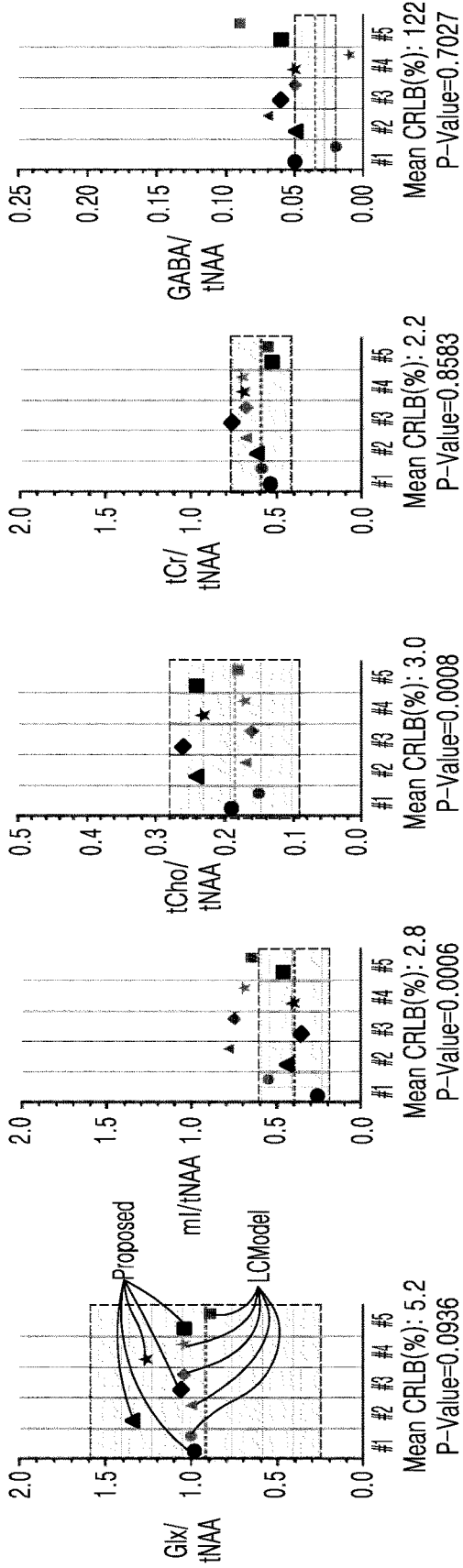
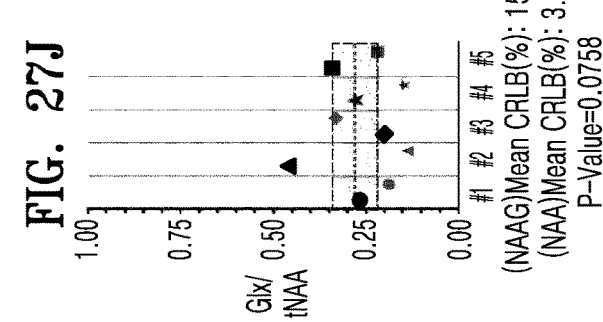

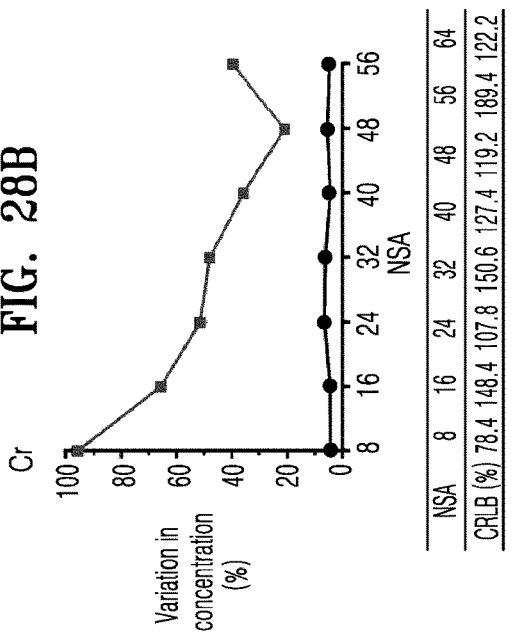
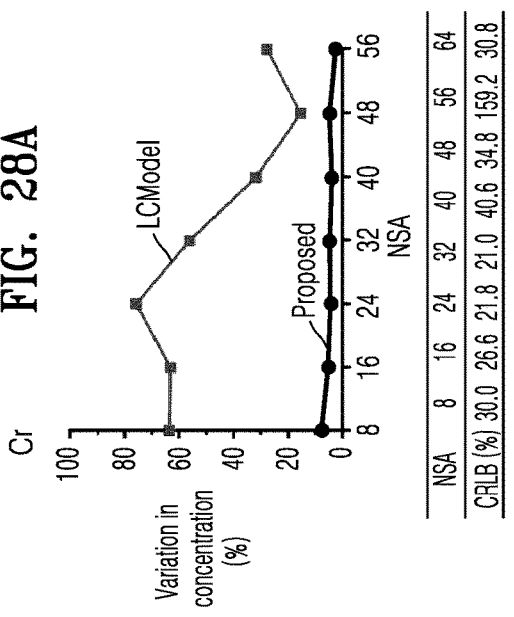
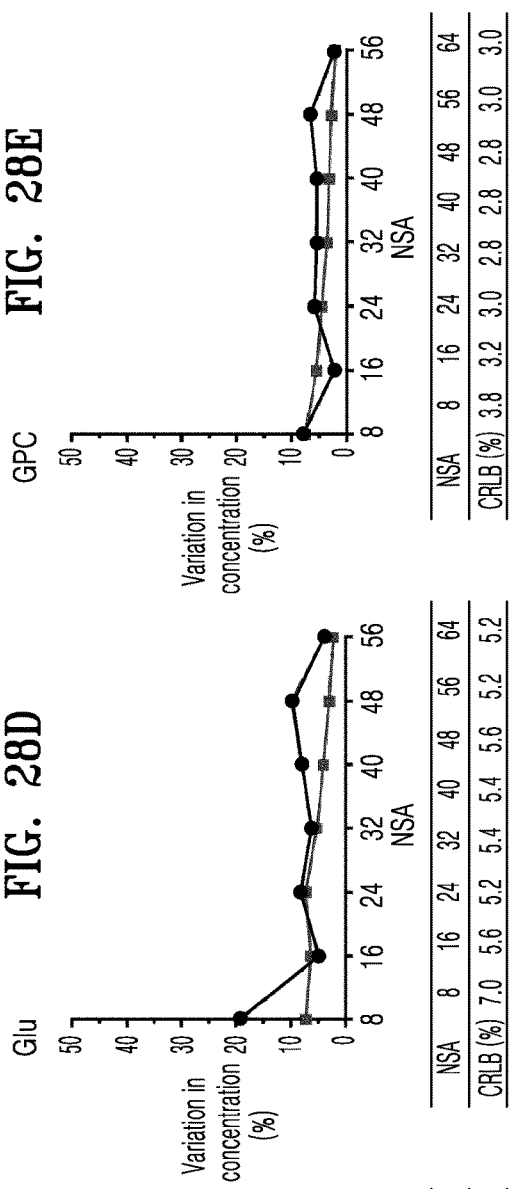

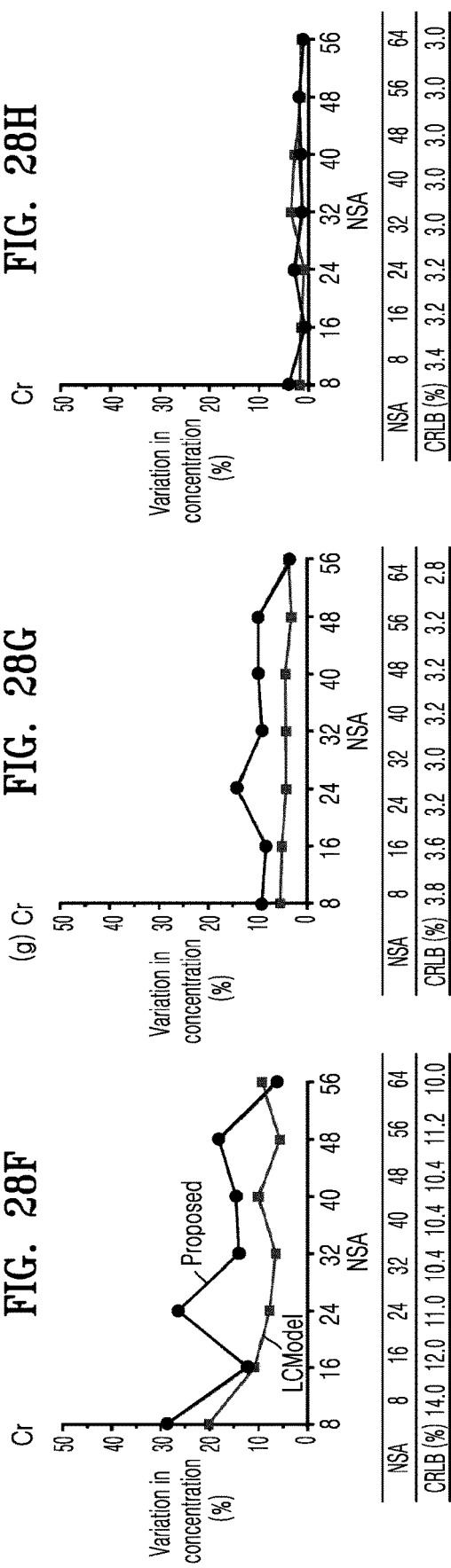
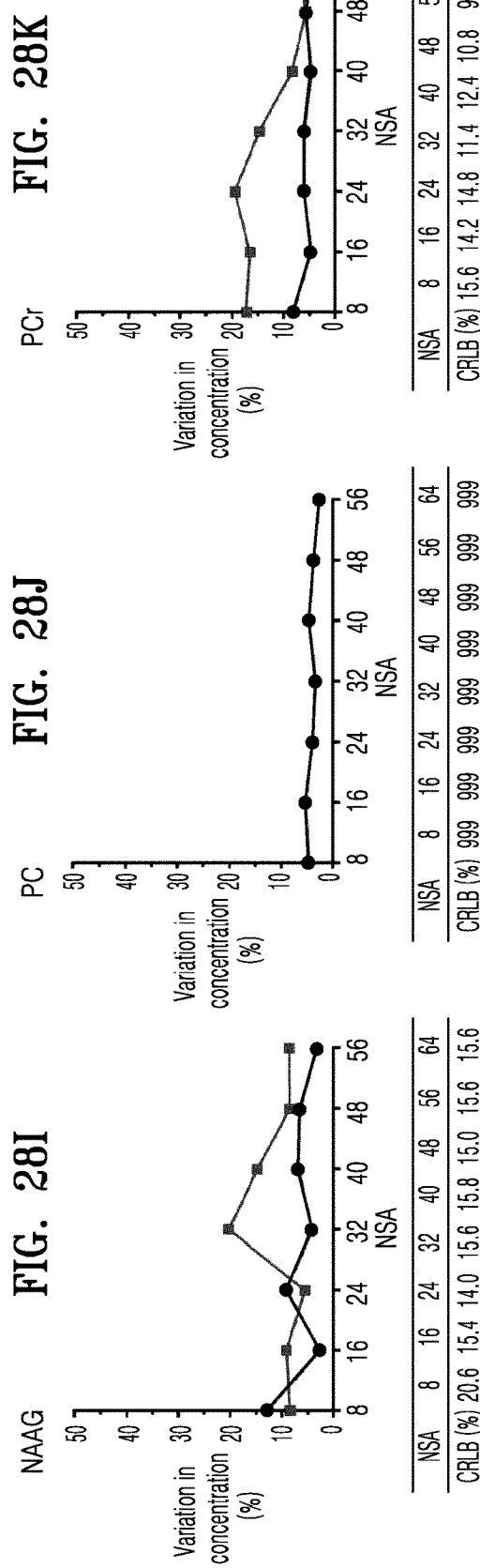
FIG. 28F  FIG. 28G  FIG. 28H
FIG. 28I  FIG. 28J  FIG. 28K

FIG. 30

| Patient ID | Gene sequencing results | DNN results | LCModel results |
|---|---|---|---|
| 1 | Mutant | 2HG – negative | 2HG – negative |
| 2 | Mutant | 2HG – positive | 2HG – negative |
| 3 | Mutant | 2HG – positive | 2HG – negative |
| 4 | Mutant | 2HG – positive | 2HG – negative |
| 5 | Mutant | 2HG – positive | 2HG – positive |
| 6 | Mutant | 2HG – positive | 2HG – negative |
| 7 | Wild type | 2HG – negative | 2HG – negative |
| 8 | Wild type | 2HG – negative | 2HG – negative |
| 9 | Wild type | 2HG – negative | 2HG – negative |
| 10 | Wild type | 2HG – negative | 2HG – negative |
| 11 | Mutant | 2HG – negative | 2HG – negative |
| 12 | Wild type | 2HG – positive | 2HG – positive |
| 13 | Wild type | 2HG – negative | 2HG – negative |

FIG. 32

```
--------------------------------------------------
Spectrum # 0 Quantification results
* quantification lower/upper limit error(%): -10.44 % 13.03 %
 * actual quantification error(PRED/GT signal %): [2.84] %
--------------------------------------------------

--------------------------------------------------
Spectrum # 1 Quantification results
* quantification lower/upper limit error(%): -10.44 % 2.62 %
 * actual quantification error(PRED/GT signal %): [-1.69] %
--------------------------------------------------
```

ARTIFICIAL NEURAL NETWORK-BASED NUCLEAR MAGNETIC RESONANCE AND MAGNETIC RESONANCE SPECTROSCOPY DATA PROCESSING METHOD AND APPARATUS THEREOF

TECHNICAL FIELD

The present disclosure relates to a method and apparatus for processing, based on an artificial neural network, nuclear magnetic resonance and magnetic resonance spectroscopy data obtained using a magnetic resonator.

BACKGROUND ART

Magnetic Resonance Spectroscopy (MRS) is a technique to obtain metabolomics information non-invasively by applying a Nuclear Magnetic Resonance (NMR) method to a living body, and has high application potential in basic research and clinical practice.

However, MRS has a limited degree of accuracy in metabolite quantitative analysis because of various causes such as a low brain metabolite concentration, a low signal-to-noise ratio caused by a weak magnetic field, overlap between metabolite signals due to a weak magnetic field, and overlap between basal and metabolite signals.

Therefore, there is a need to improve the overall quality of NMR or MRS data, improve the accuracy of metabolite quantitative analysis using NMR and MRS data, and provide techniques for diagnosing various diseases.

The above-described background art is technical information that the inventors had or learned when or while deriving the present disclosure and may not be publicly known before the filing of the present application.

DESCRIPTION OF EMBODIMENTS

Technical Problem

1) SNR, Linewidth Narrowing, and Spectral Baseline Removal Which are Related to MRS Metabolite Quantification Technology An embodiment of the present disclosure provides a method and apparatus for processing nuclear magnetic resonance (NMR) and magnetic resonance spectroscopy (MRS) data based on an artificial neural network with improved quantification accuracy compared to the existing methods used to metabolite quantification analysis of NMR/MRS data by developing an artificial neural network capable of addressing low SNR, line-broadening, and spectral baselines which limit MRS-based metabolite quantification technology by increasing the SNR of data, implementing line-narrowing performance, and removing spectral baselines.

2) Providing Algorithms for Improving Reliability of Results of Data Processing

Another embodiment of the present disclosure provides a method and apparatus for processing NMR and MRS data based on an artificial neural network by providing an algorithm for providing a percentage absolute error rate indicating the reliability of results of processing data of which true values are unknown, instead of providing CRLB which is currently most widely used but may eventually cause prejudice in analysis of results because CRLB shows the precision, not accuracy, of results of quantification, such that a user may appropriately interpret results of corresponding data analysis.

3) High-Quality Spectrum Recovery in FID, and Screening of Bad Data

Another embodiment of the present disclosure provides an artificial neural network apparatus using a technique of reconstructing a high-quality spectrum from incomplete data and a technique of screening bad data.

Another embodiment of the present disclosure provides an artificial neural network apparatus capable of diagnosing various troubles/diseases from data.

Solution To Problem

A preferred embodiment of the present disclosure provides a method of diagnosing a disease using nuclear magnetic resonance and magnetic resonance spectroscopy, the method including: receiving, by a data input unit, input data from a magnetic resonator; defining, by the data input unit, incomplete data from the input data based on a sampling time of the input data and determining, by the data input unit, whether remaining data of the input data except the incomplete data is bad data not satisfying a preset criterion; receiving and recovering, by a data recovery unit, the incomplete data and the bad data; and analyzing, by a disease diagnosis unit, metabolite-specific quantification data based on a metabolite concentration range by receiving a ground truth data from the data input unit and receiving the recovered incomplete data from the data recovery unit or only a recovered portion of the bad data from the data recovery unit.

Preferably, the defining of the incomplete data is performed based on a header of the input data. In more detail, the defining of the incomplete data is performed based on a sampling time which is calculated using a data point value of the header.

Preferably, the determining of the bad data is performed based on artifacts detected from the FFT of remaining data of the input data that is not defined as the incomplete data.

According to an embodiment of the present disclosure, a method of detecting a target metabolite using a computing apparatus may include: obtaining biological data from a magnetic resonator; extracting incomplete data including at least one truncated section by inputting the biological data into a signal failure determination model; obtaining recovered data, in which the truncated section is recovered, by inputting the incomplete data into a first neural network; obtaining metabolite-specific quantification data based on a metabolite concentration range by inputting the recovered data into a second neural network; and obtaining results of target metabolite detection by inputting the recovered data and the metabolite-specific quantification data into a third neural network.

In an embodiment, the biological data may include ground truth data having no truncated section, the incomplete data, and bad data; the extracting of the incomplete data may include removing the bad data included in the biological data; and the obtaining of the results of the target metabolite detection may include obtaining the results of the target metabolite detection by additionally inputting the ground truth data into the third neural network.

In an embodiment, the obtaining of the biological data may include obtaining a metabolite signal from the magnetic resonator and obtaining a plurality of pieces of biological data by changing a signal element of the obtained metabolite signal, wherein the signal element may include at least one selected from the group consisting of signal linewidth, phase, frequency, and signal-to-noise ratio.

In an embodiment, the extracting of the incomplete data may include extracting the incomplete data by comparing a sampling time of the biological data with a reference sampling time at the magnetic field strength of the biological data by using the signal failure determination model.

In an embodiment, the obtaining of the recovered data may include dividing the incomplete data into designated units and inputting the divided incomplete data into the first neural network to obtain the recovered data.

In an embodiment, the obtaining of the metabolite-specific quantification data may include performing fast Fourier transform (FFT) on the recovered data and inputting the transformed recovered data into the second neural network having a CNN structure to obtain the metabolite-specific quantification data, wherein the metabolite-specific quantification data may include concentration data for each section of a plurality of metabolites.

In an embodiment, the results of the target metabolite detection may include concentration data of the target metabolite, wherein the obtaining of the results of the target metabolite detection may include determining that the target metabolite is detected in the biological data when the concentration data of the target metabolite exceeds a given reference, and generating pathological diagnosis data based on the target metabolite.

According to another embodiment of the present disclosure, a target metabolite detection apparatus may include a processor, wherein the processor may obtain biological data from a magnetic resonator, extract incomplete data including at least one truncated section by inputting the biological data into a signal failure determination model, obtain recovered data, in which the truncated section is recovered, by inputting the incomplete data into a first neural network, obtain metabolite-specific quantification data based on a metabolite concentration range by inputting the recovered data into a second neural network, and obtain results of target metabolite detection by inputting the recovered data and the metabolite-specific quantification data into a third neural network.

In an embodiment, the biological data may include ground truth data having no truncated section, the incomplete data, and bad data, and the processor may remove the bad data included in the biological data, and may obtain the results of the target metabolite detection by additionally inputting the ground truth data into the third neural network.

In an embodiment, the results of the target metabolite detection may include concentration data of the target metabolite, wherein the processor may determine that the target metabolite is detected in the biological data when the concentration data of the target metabolite exceeds a given reference, and may generate pathological diagnosis data based on the target metabolite.

Other aspects, features, and advantages will become apparent and more readily appreciated from the accompanying drawings, claims, and detailed description.

Advantageous Effects of Disclosure

Another embodiment of the present disclosure provides an artificial neural network apparatus using a technique of reconstructing a high-quality spectrum from incomplete data and a technique of screening bad data.

Another embodiment of the present disclosure provides an artificial neural network apparatus capable of diagnosing various troubles/diseases from data.

BRIEF DESCRIPTION OF DRAWINGS

FIG. 16 is a view illustrating original data obtained from a rat with a brain tumor lesion and data recovered after FID-truncation, according to an embodiment of the present disclosure.

FIG. 17 is a view illustrating original data obtained from a normal rat and data recovered after FID-truncation, according to an embodiment of the present disclosure.

FIG. 21 is a view illustrating MAE for each metabolite in 10,000 test sets, according to an embodiment of the present disclosure.

FIGS. 27A-27J illustrate results of metabolite-specific quantification according to an embodiment of the present disclosure together with LCM results.

FIGS. 28A-28K illustrate graphs showing the absolute difference between results of quantification of NSA 64 data and results of quantification of NSA 8-56 data, according to an embodiment of the present disclosure.

FIG. 30 is a view illustrating 2HG-positive/2HG-negative diagnostic results for a group of 13 patients, according to an embodiment of the present disclosure.

FIG. 32 is a view illustrating displaying of errors predicted for results of metabolite quantification of data included in a test set, according to an embodiment of the present disclosure.

MODE OF DISCLOSURE

Figure 1:
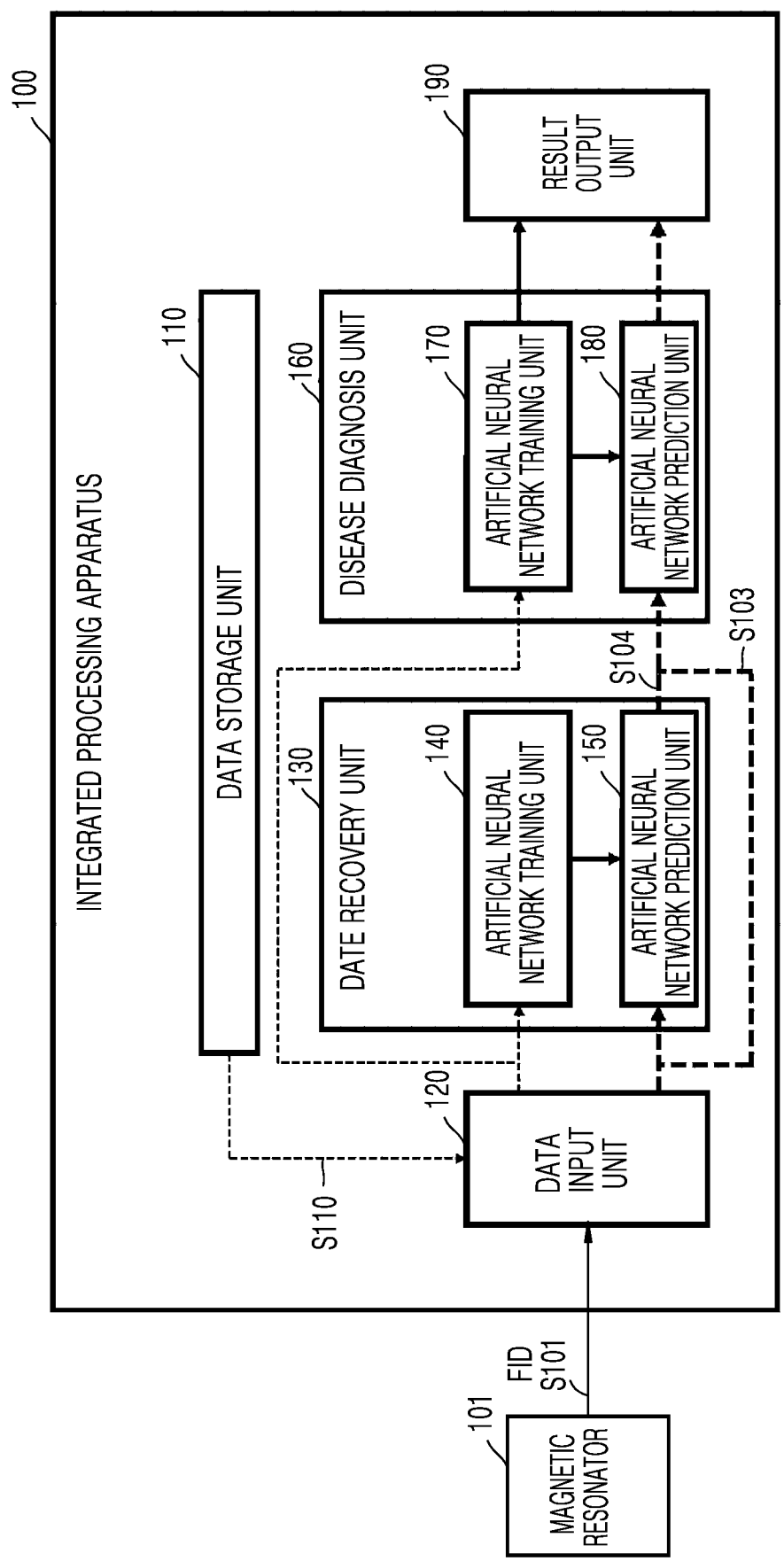
FIG. 1 is a view illustrating an internal configuration of an apparatus for processing nuclear magnetic resonance (NMR) and magnetic resonance spectroscopy (MRS) data based on an artificial neural network according to an embodiment of the present disclosure.

Reference will now be made in detail to the embodiments of the present disclosure, examples of which are illustrated in the accompanying drawings. These embodiments are described in sufficient detail to enable those of ordinary skill in the art to practice the present disclosure. It should be understood that the various embodiments of the present disclosure are different from each other but need not be mutually exclusive. For example, in the present disclosure, certain shapes, structures, and features described in one embodiment may be modified in another without departing from the spirit and scope of the present disclosure. In addition, it should be understood that the positions or arrangement of individual components within each embodiment may be changed without departing from the spirit and scope of the present disclosure. Therefore, the following detailed description should not be considered in a limiting sense, but should be considered as encompassing the claims and all equivalents thereof. In the drawings, like reference numerals refer to the same or similar elements in various aspects.

In the present disclosure, the term "artificial intelligence (AI)" may refer to AI or a field of research into methods of implanting AI, the term "machine learning" may refer to a field of AI technology that enables computing devices to learn from data to understand specific objects or conditions, or may refer to algorithms which enable computers to analyze data as technical methods for finding and classifying patterns in data. Machine learning disclosed in the present disclosure may be understood as including an operation method for training an AI model.

Hereinafter, various embodiments of the present disclosure will be described in detail with reference to the accompanying drawings, so that those of ordinary skill in the art may clearly understand the scope of the present disclosure.

FIG. 1 is a view illustrating an internal configuration of an apparatus for processing nuclear magnetic resonance (NMR) and magnetic resonance spectroscopy (MRS) data based on an artificial neural network according to an embodiment of the present disclosure.

However, the configuration view shown in FIG. 1 is only an example illustrating the apparatus for processing NMR and MRS data based on an artificial neural network, and the internal configuration of the apparatus for processing NMR and MRS data based on an artificial neural network according to some embodiments of the present disclosure is not limited to the illustrated configuration.

Hereinafter, the types and formats of data described in the present specification are not limited. For example, data described below may include NMR/MRS time-domain raw data (for example, Free Induction Decay: hereinafter referred to as FID), frequency-domain spectral data represented using Fourier Transform, and data on nuclides such as 1H, 13C, 19F, and 31P.

NMR+MRS integrated processing apparatus 100.

A method of processing NMR and MRS data based on an artificial neural network according to an embodiment of the present disclosure may be performed by an integrated processing apparatus 100 for NMR and MRS. According to an embodiment, the integrated processing apparatus 100 may include a data storage unit 110, a data input unit 120, a data recovery unit 130, a disease diagnosis unit 160, and a result output unit 190. Furthermore, in some embodiments, the data recovery unit 130 and the disease diagnosis unit 160 may include artificial neural network training units 140 and 170 and artificial neural network prediction units 150 and 180, respectively.

The data storage unit 110 may store training data for artificial neural networks. For example, the data storage unit 110 may store data which is obtained from living bodies or samples collected from normal people, patients, and animal models related to various diseases by using a magnetic resonator or may store simulation data thereof. Moreover, the data storage unit 110 may store incompletely obtained data or partially selected data. The incompletely obtained data includes truncated data and undersampled data.

In one embodiment, the simulation data may be obtained by simulating data in consideration of all of various ratios of concentrations of major metabolites that may exist in each organ (brain, liver, muscle, heart, etc.) of the body, data quality determinants, data acquisition parameters, quantum physical properties of metabolites.

The quality of data stored in the data storage unit 110 may be determined based on at least one selected from the group consisting of magnetic field strength, signal-to-noise ratio, linewidth, spectral baseline, phase shift, frequency shift, ghosting artifact (unwanted signal), and residue water signal. The data acquisition parameters may include at least one selected from the group consisting of pulse sequence types, characteristics of high frequency pulses (RF) forming a pulse sequence, gradient magnetic field characteristics, echo time (TE), and repetition time (TR). In addition, the quantum physical properties of metabolites may include the longitudinal relaxation time T1 of metabolites, the transverse time T2 of metabolites, J-coupling, and spin information on metabolites. The data storage unit 110 according to the present embodiment may store training data for artificial neural networks and may store a metabolite relative concentration ratio, a quality determinant, and a data acquisition parameter which correspond to each piece of data.

The data input unit 120 may obtain input data S110 from the data storage unit 110 or input data S101 from a magnetic resonator 101.

The data input unit 120 may determine, based on the type of the input data S101 and S110, whether to transmit the input data S101 and S110 to the data recovery unit 130 or the disease diagnosis unit 160.

In another embodiment, even when input data S110 for training is classified as incomplete/bad data, the complete form (hereinafter referred to as ground truth data) of the input data S110 and header information on the input data S110 may be transmitted together and may be used by the data recovery unit 130 and the disease diagnosis unit 160 in accordance with training purposes. Note that when input data S101 is classified as incomplete/bad data S102, only a header including parameters is transmitted to the data recovery unit 130 together with the input data S101. Ground truth data S103 is transmitted to the disease diagnosis unit 160.

When the data acquisition time of input data S101 is less than a preset time, the data input unit 120 classifies the input data S101 as incomplete data. In addition, it may be determined whether data which is not classified as incomplete data among the input data S101 is bad data or not, and when it is determined that the data is not bad data, the data may be classified as ground truth data.

Figure 10:
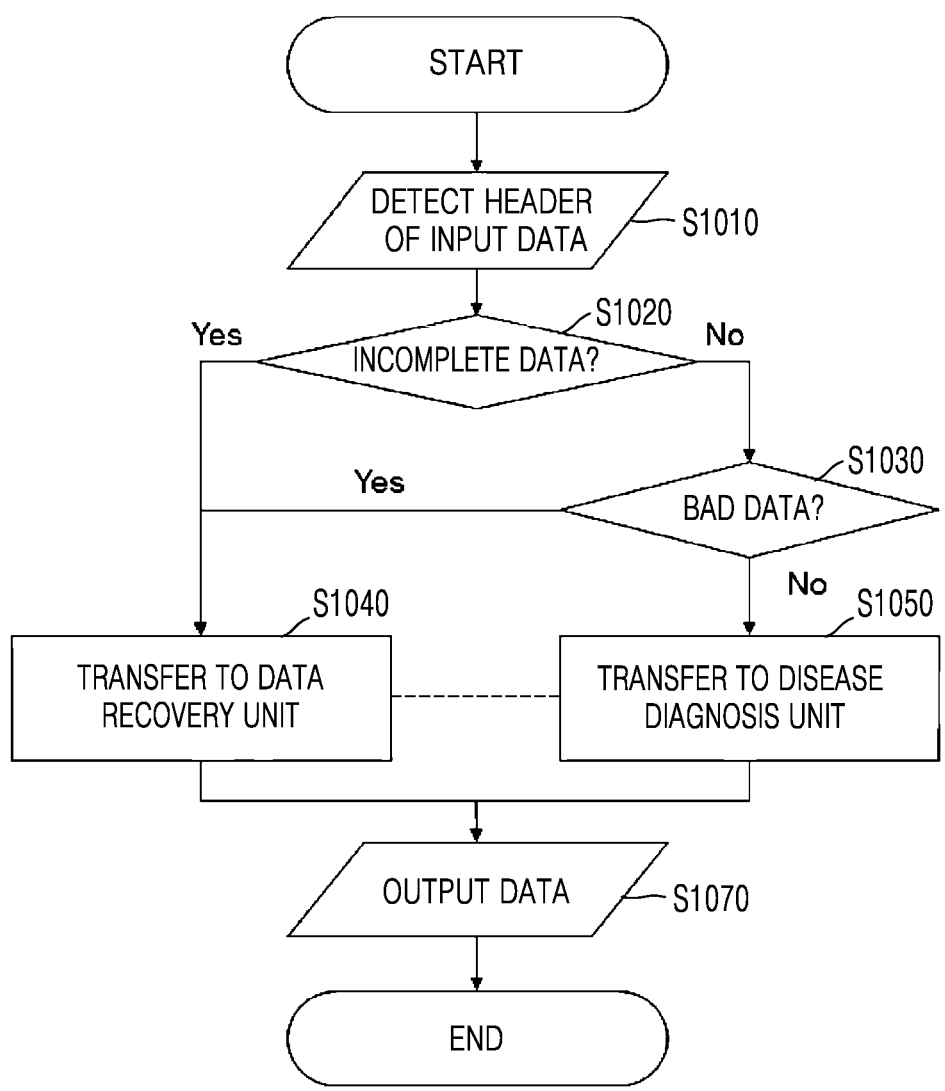
FIG. 10 is a flowchart illustrating a processing method for a data input unit according to an embodiment of the present disclosure.

Referring to FIG. 10, the data input unit 120 may extract parameters from the header of input data S110 and S101 (S1010). The parameters may include at least one selected from the group consisting of magnetic field strength B0, the number of data points, and spectral bandwidth (SW).

The data input unit 120 determines, based on data point values in the header, whether the input data is incomplete data (S1020). Specifically, the criterion, based on which the vision data input unit 120 determines incompleteness, is a sampling time (sec) which may be extracted as a data point value (1/SW). For example, the minimum acquisition time at a magnetic field strength of 3 T may be 0.512 sec (1024 data points, SW=2000 Hz), and a reference acquisition time at a magnetic field strength of 9.4 T may be 0.256 sec (1024 data points, SW=5000 Hz).

In one embodiment, when the sampling time of the input data is shorter than a reference sampling time tm at a given magnetic field strength by 50% or less, the data input unit 120 may determine the input data as incomplete data, and when the sampling time of the input data exceeds the reference sampling time tm at the given magnetic field strength, the data input unit 120 may determine the input data as ground truth data (S1020).

When the input data is determined as ground truth data, the data input unit 120 additionally determines whether the input data is bad data (S1030).

The criterion for determining bad data may whether there any artifact element other than metabolites or baseline signals is additionally present within the range of 0.5 ppm to 4.5 ppm in the FFT form of the input data. For example, whether an artifact element is included in a signal may be determined by change point detection cumulative sum (CUSUM). In addition, bad data refers to data having quality that does not satisfy a criterion which is preset for training an artificial neural network.

When the data input to the data input unit 120 is classified as incomplete data or bad data, the data is transmitted to the data recovery unit 130 (S1040). Other ground truth data is transmitted to the disease diagnosis unit 160 (S1050). After that, diagnosis of diseases is performed, and data is output (S1070).

The data recovery unit 130 may recover incomplete data into ground truth data and may exclude bad data. The data recovery unit 130 may use various neural networks, such as a convolutional neural network and a recurrent neural network.

In a preferred embodiment of the present disclosure, when data transmitted from the data input unit 120 to the date recovery unit 130 is incomplete or bad, the date recovery unit 130 recovers the data or determines that the data is not analyzable. To this end, the data recovery unit 130 includes the artificial neural network training unit 140 and the artificial neural network prediction unit 150.

Figure 11:
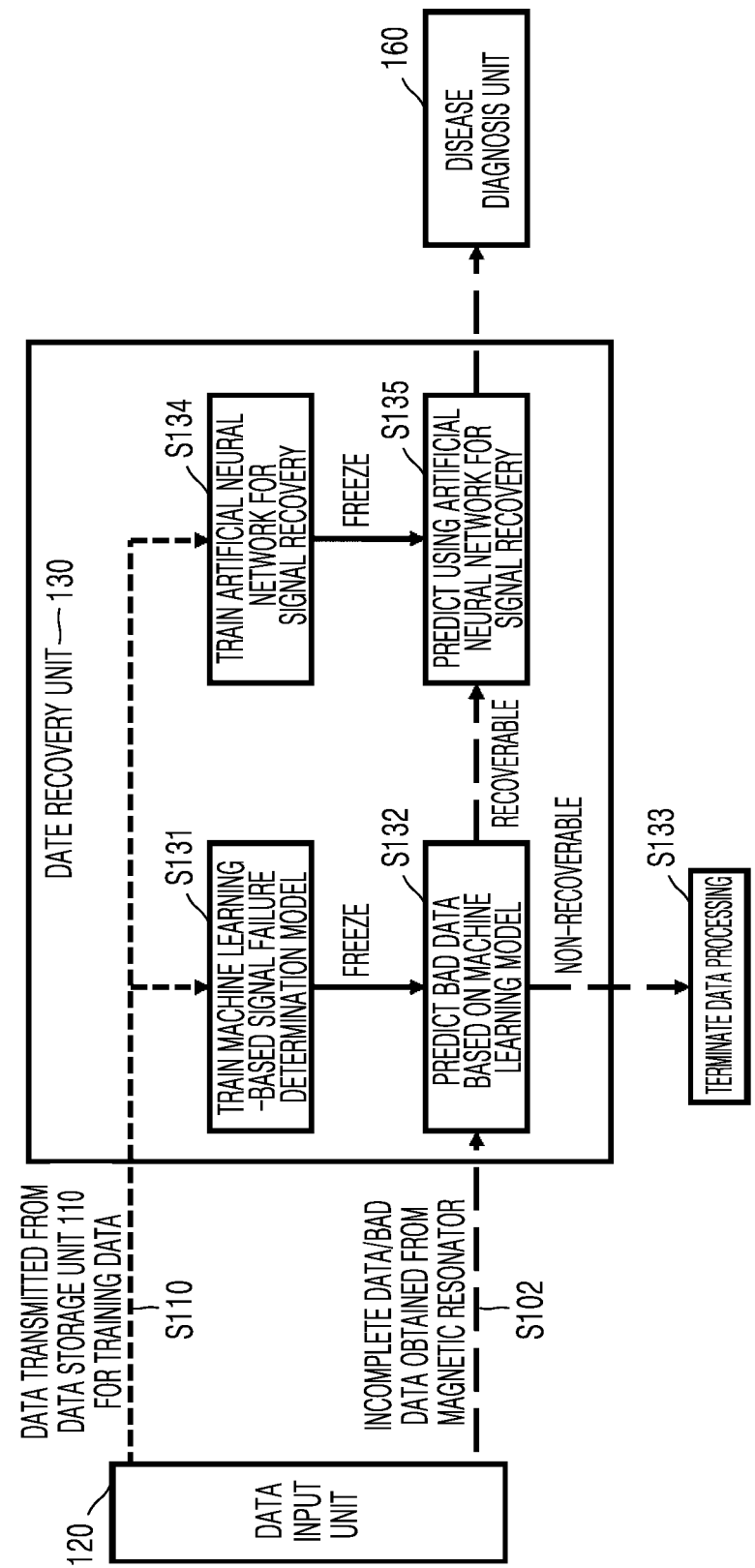
FIG. 11 illustrates functions of components of a data recovery unit that performs a data integrity test and data recovery according to an embodiment of the present disclosure.

Referring to FIG. 11, the artificial neural network training unit 140 performs training (S131) for determining whether data is bad data by performing machine learning based on an input signal S110 which the data input unit 120 has received from the data storage unit 110, and based on this, it is predicted whether input data S102 is bad data (S132). When the input data S102 is unrecoverable bad data, data processing is terminated (S133).

In a preferred embodiment of the present disclosure, the artificial neural network training unit 140 may perform supervised learning by using a pair of incomplete data and ground truth data (for example, ground truth data) which are required for training. In this case, data quality may be improved by denoising or the like during a learning process of an artificial neural network unit.

The input data S110 input to the artificial neural network training unit 140 may be classified into training data and testing data, or into training data, verification data, and testing data. When the training of an artificial neural network is completed, the artificial neural network training unit 140 may freeze the trained artificial neural network and deliver the trained artificial neural network to the artificial neural network prediction unit 150. Here, in case of bad data, the bad data may be tagged with a message saying "Impossible to process" and may be transmitted without additional data processing.

The artificial neural network training unit 140 may include a machine learning-based signal failure determination model which determines quality control criteria by using input data S110 received from the data storage unit 110.

The type of artificial neural network model is not limited, but a machine learning-based support vector machine (SVM) model or the like may be used, and data quality determining factors may include at least one selected from the group consisting of ghosting, residual water signal, linewidth, or SNR. Hereinafter, for ease of understanding of the present disclosure, the following description is given under the assumption that the signal failure determination model is an SVM model, but it should be noted that the present disclosure is not limited thereto.

The artificial neural network prediction unit 150 receives the artificial neural network trained by the artificial neural network training unit 140 and determines whether FID input signal S102 received from the data input unit is bad data or incomplete data.

The artificial neural network prediction unit 150 may use the artificial neural network received from the artificial neural network training unit 140 to recover incomplete data S102 which is obtained from an actual magnetic resonator and does not include ground truth data. Recovered data may be transferred to the artificial neural network prediction unit 180 of the disease diagnosis unit 160 to quantify metabolites or diagnose diseases by using the recovered data. Although the work of recovering data and the work of diagnosing diseases based on metabolites have been separately performed in the related art, the date recovery unit 130 and the disease diagnosis unit 160 are integrated in the integrated processing apparatus 100 according to a preferred embodiment of the present disclosure, and thus it is advantageous in that the date recovery unit 130 recovers incomplete data, the artificial neural network prediction unit 180 receives the data and quantifies metabolites or diagnose diseases by using the data, and results of these sequential processes are automatically provided through the result output unit 190.

The disease diagnosis unit 160 may perform metabolite quantification or disease diagnosis. More specifically, the disease diagnosis unit 160 may express the amount of a metabolite in input data as an absolute concentration or a relative concentration. In addition, it is possible to categorize and classify data into sections according to the concentration of a specific metabolite.

In addition, the disease diagnosis unit 160 may diagnose diseases based on ground truth data S103 directly received from the data input unit 120, recovered data S104 received from the data recovery unit 130, or results of quantification of metabolites.

The disease diagnosis unit 160 may include the artificial neural network training unit 170 and the artificial neural network prediction unit 180. The artificial neural network training unit 170 may perform data quality processing and metabolite quantification by using an artificial neural network, or may classify data into sections according to the concentration of a specific metabolite.

The structure of the artificial neural network is not limited, and various neural networks such as a convolutional neural network or a stacked autoencoder may be used. As artificial neural network training data, ground truth data, metabolite concentrations, relative concentrations, or section values of the concentration of a specific metabolite may each be paired and may be used for supervised learning or unsupervised learning. The quality of input data may be improved through a training process by the artificial neural network training unit 170. The above-described input data of an artificial neural network may be classified into training data and testing data, or into training data, verification data, and testing data. Thereafter, the artificial neural network that has been completely trained by the artificial neural network training unit 170 may be frozen and transferred to the artificial neural network prediction unit 180.

The artificial neural network prediction unit 180 uses the artificial neural network received from the artificial neural network training unit 170 to improve the quality of data, which is obtained from an actual magnetic resonator and does not include ground truth data, by perform denoising, line-narrowing, frequency adjustment, and phase adjustment on the data.

In addition, the artificial neural network prediction unit 180 may edit the data, calculate section values (classifications) of the concentration of a specific metabolite, or diagnose diseases. After being completely processed, the data may be transmitted to the result output unit 190.

The result output unit 190 may extract the concentration/relative concentration of a metabolite through a linear algebra calculation from data or edited data received from the artificial neural network training unit 170 or the artificial neural network prediction unit 180, and may output the rate of errors thereof.

Although statistical errors occur in the related art because of the use of CRLB indicating the accuracy of metabolite quantification, the present disclosure is advantageous in that the reliability of results of metabolite quantitative data is improved by outputting the rate of errors which indicates absolute errors relative to predicted values.

In an embodiment, the result output unit 190 may calculate absolute errors before results of the artificial neural network prediction unit 180 are displayed. More specifically, because data received from the artificial neural network training unit 170 has a true value for concentration/relative concentration, the result output unit 190 may use the true value to previously perform the process of calculating an absolute error by considering the data quality of the data input unit 120 and received data. Thereafter, the result output unit 190 may determine an expected absolute error rate for results of the artificial neural network prediction unit 180. In another embodiment, the result output unit 190 may output data without determining the rate of errors for results of section values of concentration ranges.

Hereinafter, operations of the components, which are included in the apparatus for processing NMR and MRS data based on an artificial neural network shown in FIG. 1, will be described in detail with reference to FIGS. 2 to 32.

FIGS. 2 to 9 are views illustrating the operation of the data storage unit 110 in detail according to an embodiment of the present disclosure.

According to an embodiment, the data storage unit 110 may acquire a model metabolite signal (model metabolite basis set) by measuring a sample or performing a quantum mechanical calculation.

Hereinafter, how the data storage unit 110 acquires a model metabolite signal by measuring a sample will be described according to an embodiment of the present disclosure.

First, the data storage unit 110 may obtain a metabolite sample. The type of metabolite sample is not limited. For example, the type of metabolite sample may include at least one selected from the group consisting of alanine (Ala), aspartate (Asp), creatine (Cr), γ-amino butyric acid (GABA), glucose (Glc), glutamine (Gln), glutamate (Glu), glutathione (GSH), glycerophosphorylcholine (GPC), lactate (Lac), myo-Inositol (ml), N-acetylaspartate (NAA), N-acetylaspartylglutamate (NAAG), phosphocreatine (PCr), phosphorylcholine (PC), phosphorylethanolamine (PE) and taurine (Tau). In some embodiments of the present disclosure, the metabolite sample prepared for each metabolite at a concentration of 50 mT and a pH of 7.0 to 7.5 in a 300 mL cylindrical vial (for 3.0 T magnetic resonance measurement) or a 15 ml centrifugal tube (for 9.4 T small animal magnetic resonance measurement) together with 3-trimethylsilyl-propionic acid (TSP; 1 mM) and sodium azide (NaN3; 0.1%), PC may be prepared at a concentration of 36.05 mM, and NAAG may be prepared at a concentration of 10 mM. A sample prepared as described above will be hereinafter referred to as a metabolite phantom.

Figure 2:
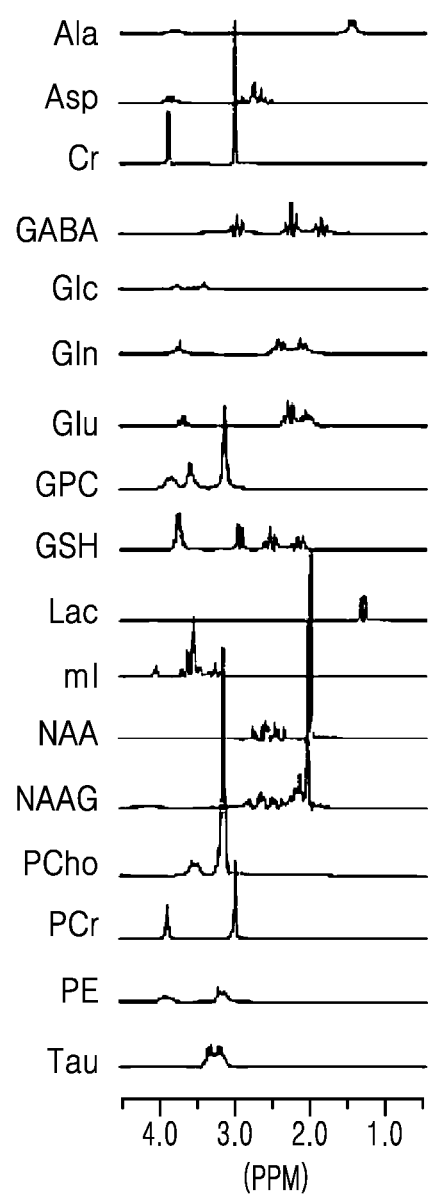
FIGS. 2 to 3 are views illustrating metabolite-specific results of Fast Fourier Transform (FFT) of data obtained at 3.0 T and 9.4 T according to an embodiment of the present disclosure.
Figure 3:
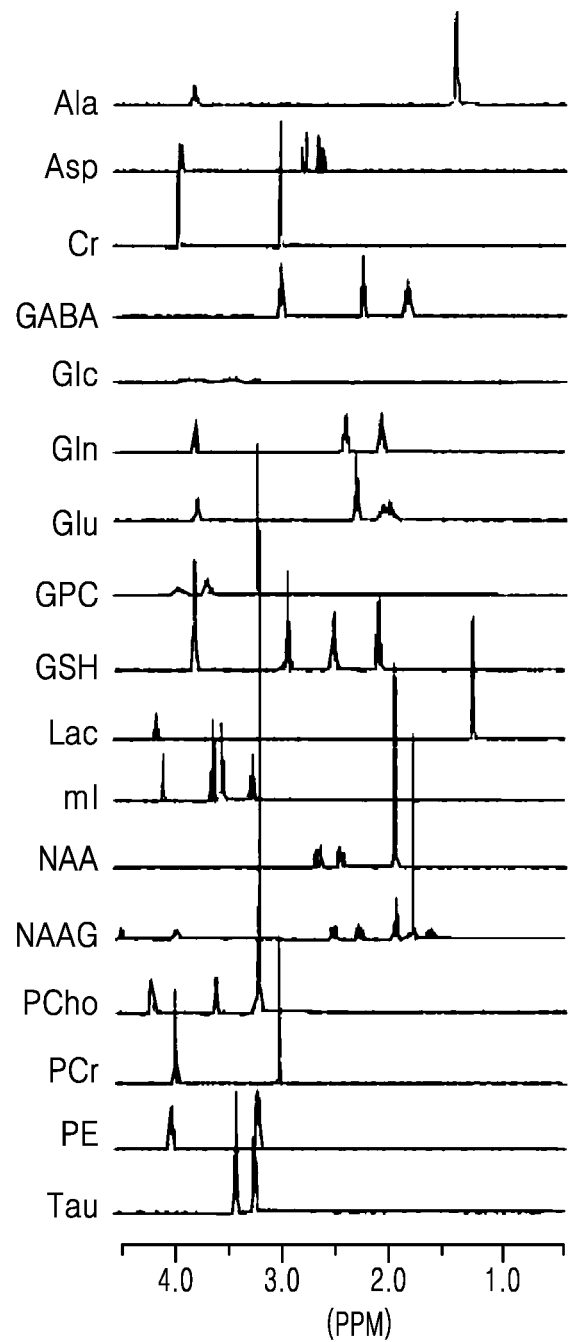

Thereafter, the data storage unit 110 may measure the prepared sample and store results thereof. FIGS. 2 and 3 are views illustrating results of Fast Fourier Transform (FFT) performed on data obtained respectively at 3.0 T and 9.4 T.

In an embodiment, a prepared metabolite phantom may be placed in a magnetic resonator, and then T2-weighted fast spin-echo images may be obtained therefrom in three axial directions. (3.0 T measurement parameters: repetition time (TR)/echo time (TE)=2000/25 ms, echo train length (ETL) =8, field of view (FOV)=200×200 mm2, matrix size=256× 256, number of slices=15 (no gap), slice thickness=8 mm, number of signal average (NSA)=1), (9.4 T measurement parameters: TR/TE=3000/30 ms, ETL=4, FOV=40×40 mm2, matrix size=256×256, number of slices=15 (no gap), slice thickness=1 mm, NSA=2).

Next, a voxel for acquiring MRS data is located on the isocenter, and then the linewidth of a water signal may be adjusted by performing first-order and second-order auto-shimming and manual shimming with respect to the voxel. (3 T reference linewidth: 5 Hz, 9.4 T reference linewidth: 3 Hz)

Data may be obtained by point resolved spectroscopy (PRESS) pulse sequence in case of a 3.0 T magnetic resonator and by spin-echo, full intensity acquired localized (SPECIAL) pulse sequence in case of a 9.4 T magnetic resonator. (3 T measurement parameters: TR/TE=4000/30 ms, spectral bandwidth (SW)=2 kHz, NSA=256, voxel size=8 cm3, number of data points=2048, zero-filled to 4096), (9.4 T measurement parameters: TR/TE=10000/3.45 ms, SW=5 kHz, NSA=256, voxel size=27 mm3 number of data points=2048, zero-filled to 4096).

Figure 4:
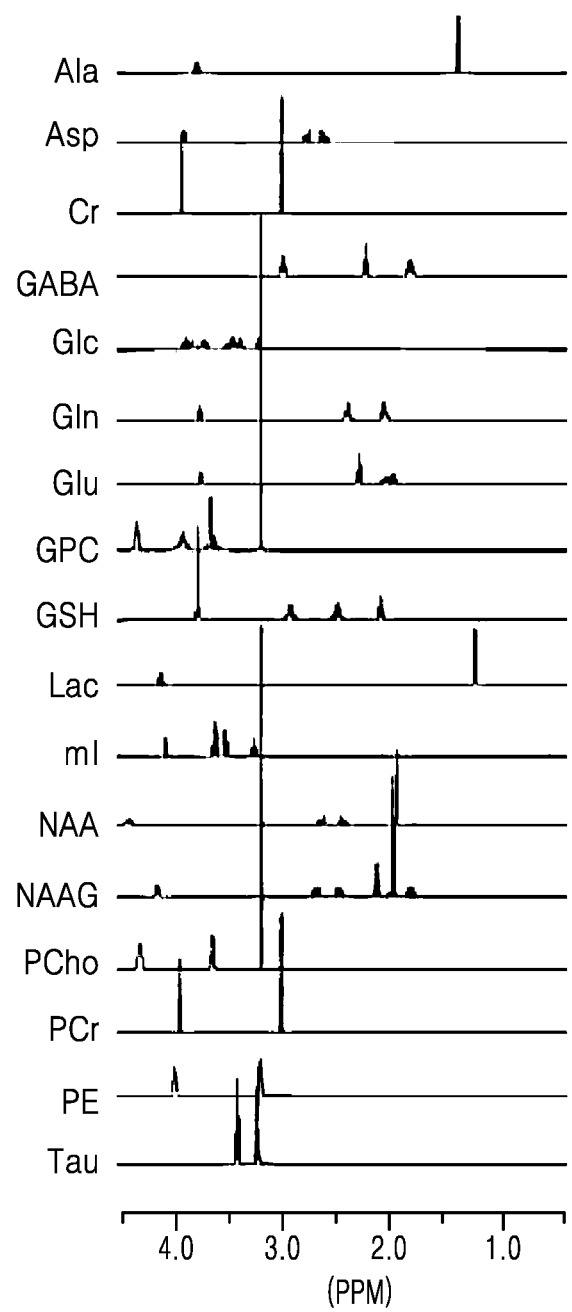
FIG. 4 is a view illustrating results of FFT of 9.4 T MRS simulated time-domain raw data according to an embodiment of the present disclosure.

How the data storage unit 110 obtains a model metabolite signal by quantum mechanical calculation will be described will be described with reference to FIG. 4 according to an embodiment of the present disclosure.

The data storage unit 110 of the present embodiment may perform a matrix product calculation (product operator) and a density matrix calculation based on chemical, quantum mechanical, spectroscopic properties (J-coupling constant, chemical shift) of the nucleons of each metabolite and pulse sequence parameters. FIG. 4 is a view illustrating results of FFT which is performed on 9.4 T MRS simulated time-domain raw data obtained through the aforementioned quantum mechanical calculation.

Thereafter, the data storage unit 110 may obtain and store biological baseline signals. More specifically, the data storage unit 110 may simulate a baseline signal that causes error in metabolite quantitative analysis of magnetic resonance data due to overlap with a metabolite signal and may include the simulated baseline signal in magnetic resonance simulation data. Although the type of baseline signal is not limited, some embodiments of the present disclosure will be described below using a baseline signal from a brain region for ease of understanding of the present disclosure.

Figure 5:
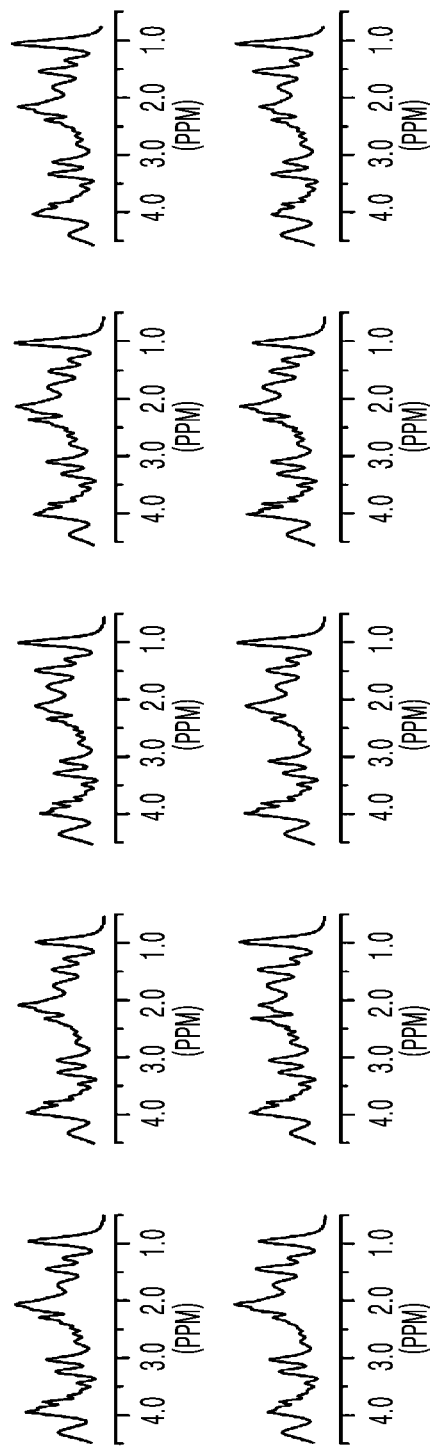
FIG. 5 is a view illustrating normal brain tissue baseline signals having various line-function spectroscopic patterns, according to an embodiment of the present disclosure.

FIG. 5 is a view illustrating normal brain tissue baseline signals (0.5 to 4.5 ppm frequency domain, 9.4 T magnetic field strength, rat brain condition) having various line-function spectral patterns. In an embodiment, the data storage unit 110 may define initial chemical shifts, signal widths, and relative amplitudes of line-functions based on prior studies to establish a baseline signal of normal brain tissue. After that, to consider irregular patterns of the baseline signal, the data storage unit 110 may establish a baseline signal having various spectral patterns by setting the relative amplitude of each line-function to be ±10% of reference value and the linewidth of each line-function to be ±20% of a reference value. In the embodiment shown in FIG. 5, the baseline signal of the human brain was simulated using 17 line-functions under a 3.0 T magnetic field condition, and the baseline signal of the rat brain was simulated using 25 line-functions under a 9.4 T magnetic field condition.

Figure 6:
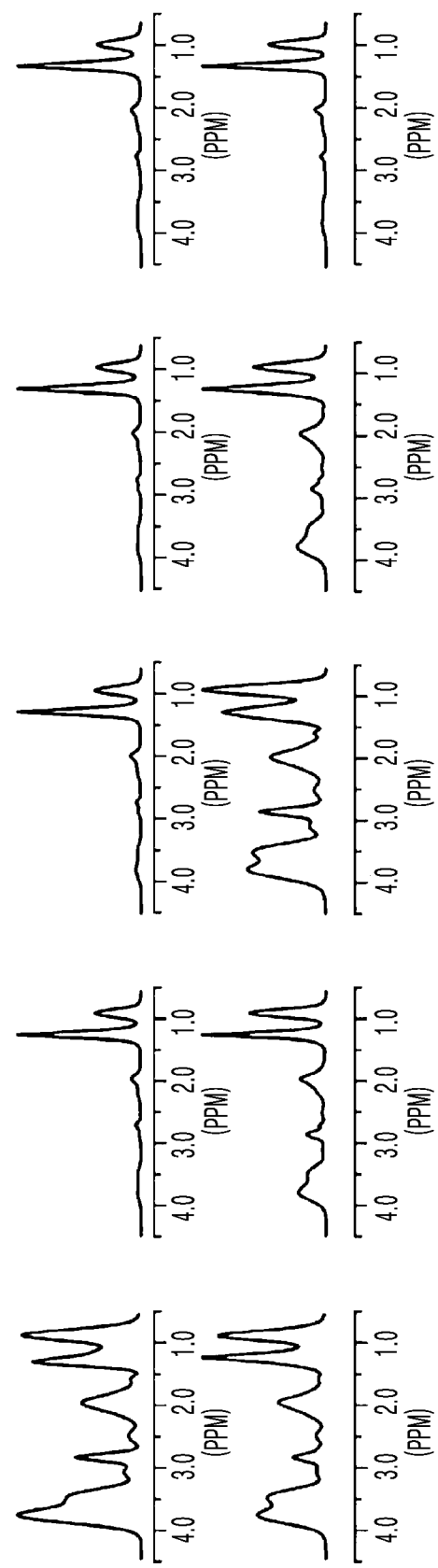
FIG. 6 is a view illustrating brain tumor tissue baseline signals having various line-function spectroscopic patterns, according to an embodiment of the present disclosure.

FIG. 6 is a view illustrating brain tumor tissue baseline signals (0.5 to 4.5 ppm frequency domain, 3.0 T magnetic field strength, human brain condition) having various line-function spectroscopic patterns.

Brain tumor tissue baseline signals having patterns which are different from those of normal brain tissue baseline signals described above are obtained, and in particular, brain tumor tissue baseline signals include fat signals. Therefore, in an embodiment, the data storage unit 110 may define initial chemical shifts, linewidths, and relative amplitudes of line-functions constituting baseline signals based on prior studies on corresponding elements. In the embodiment shown in FIG. 6, the ratio between a fat signal and a macromolecular signal such as a protein signal was adjusted for each data, and all of the other processes are assumed to be the same as in the embodiment shown in FIG. 5. Thereafter, the data storage unit 110 may store linear combinations of signal elements, signal quality adjustments, and final data.

Figure 7:
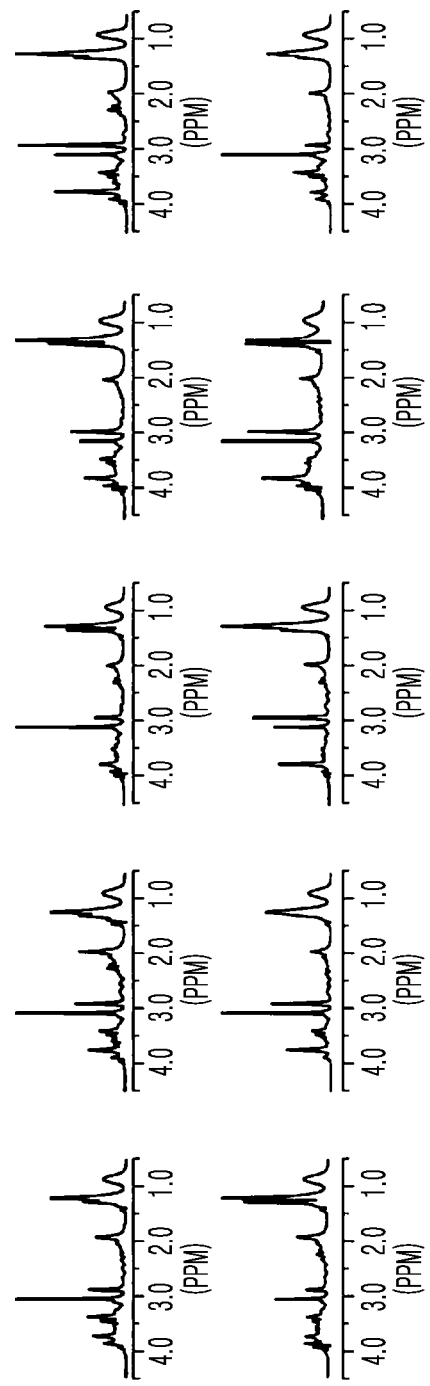
FIG. 7 is a view illustrating signals before a signal quality change during a simulation process in a brain tumor condition, according to an embodiment of the present disclosure.
Figure 8:
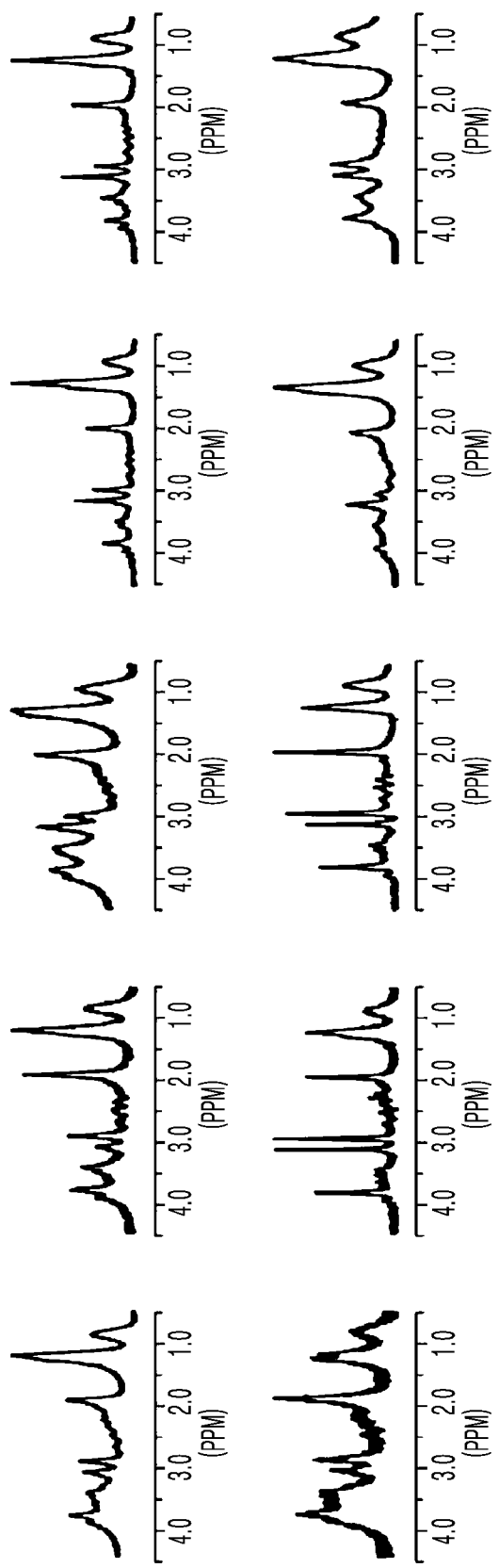
FIG. 8 is a view illustrating signals after a signal quality change during a simulation process in a brain tumor condition, according to an embodiment of the present disclosure.

FIG. 7 is a view illustrating signals (0.5 to 4.5 ppm frequency domain, 3.0 T magnetic field strength, human brain metabolite/baseline signal environment) before a signal quality change during a simulation process under brain tumor conditions according to an embodiment of the present disclosure; FIG. 8 is a view illustrating signals (0.5 to 4.5 ppm frequency domain, 3.0 T magnetic field strength, human brain metabolite/baseline signal environment) after a signal quality change during a simulation process under brain tumor conditions according to an embodiment; and FIG. 9 is a view illustrating signals (0.5 to 4.5 ppm frequency domain, 9.4 T magnetic field strength, rat brain metabolite/baseline signal environment) after a signal quality change during a simulation process under normal brain conditions according to an embodiment.

Referring to FIG. 7, the data storage unit 110 of the present embodiment may adjust the amplitudes of acquired metabolite model signals to represent various concentration combinations similar to intravital distribution conditions, and at the same time, the data storage unit 110 may perform processing to adjust the ratio of metabolite signals and baseline signals to be similar to that in vivo. Then, referring to FIGS. 8 and 9, the data storage unit 110 may finally obtain and store data to which various signal qualities, metabolite concentration combinations, and baseline signal patterns are applied by considering linewidth, phase shift, frequency shift, and signal-to-noise ratio (SNR) which are factors determining signal quality.

Figure 9:
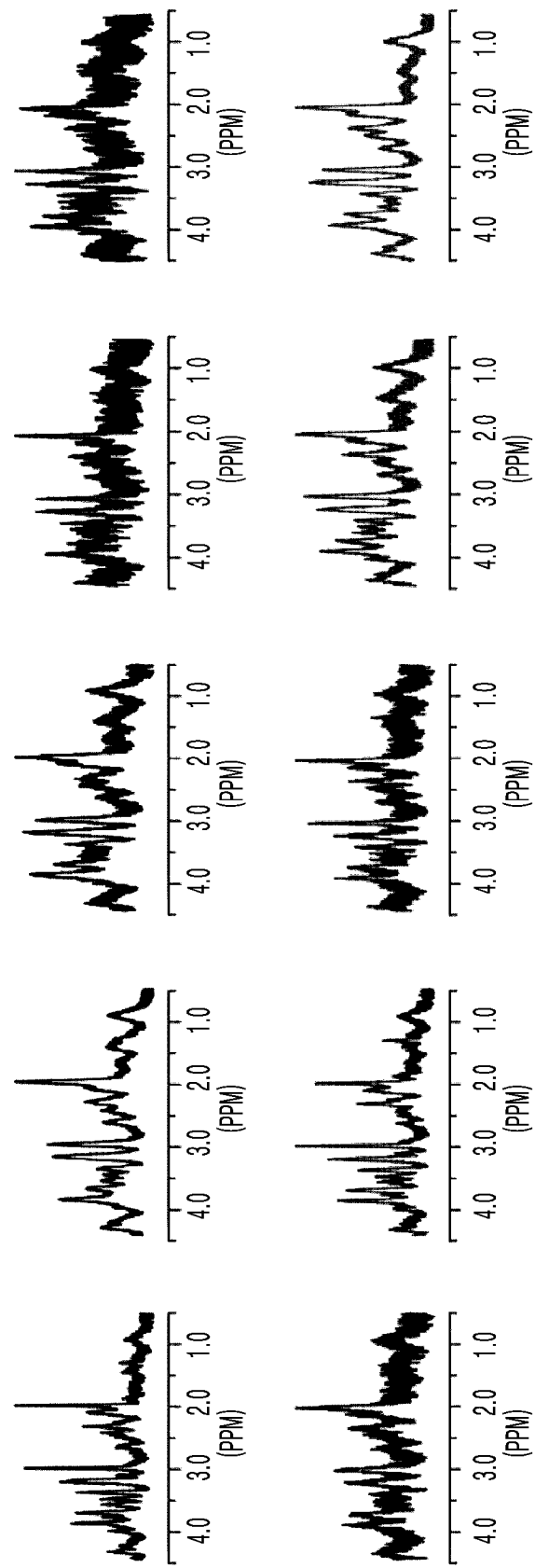
FIG. 9 is a view illustrating signals after a signal quality change during a simulation process in a normal brain condition, according to an embodiment of the present disclosure.

FIG. 8 shows signals after a signal quality change under brain tumor conditions, and FIG. 9 shows signals after a quality change induced under normal brain conditions. Thereafter, the data storage unit 110 may finally store, as raw data (FID) in a complex number format, simulation data to which all data quality factors are applied.

Figure 12:
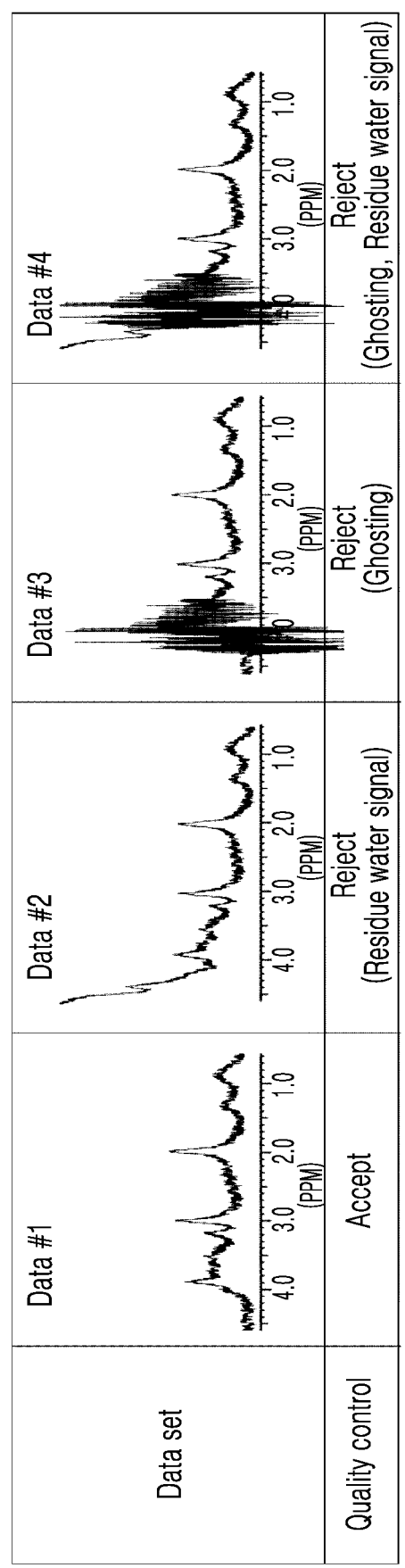
FIG. 12 is a view illustrating results of determining whether a plurality of pieces of MRS data are bad according to an embodiment of the present disclosure.

FIG. 12 is a view illustrating data as a result of determining whether a plurality of pieces of MRS data are bad data or not.

In an embodiment, a trained SVM model may be frozen, and the result of determining whether data obtained from a magnetic resonator is incomplete or bad may be output. The determination result may be either "Accept" or "Reject." Data which is determined as "Accept" is recoverable data, and a signal recovery process may be performed using a previously trained artificial neural network for recovery. Data determined as "Reject" may poor-quality or distorted data that cannot be recovered using the apparatus. In other words, recoverable data among bad data may be recovered.

That is, referring to FIG. 12, when data stored in the data storage unit 110 has unacceptably low quality or unpredictable signal elements, the data recovery unit 130 may terminate an analysis processing process without performing additional data processing and analysis processing.

In addition, the data recovery unit 130 may train an artificial neural network and perform prediction to recover data. Hereinafter, a detailed description thereof will be given with reference to FIGS. 13 to 15.

In the present embodiment, data accepted by a signal failure determination model may be recovered by an artificial neural network for signal recovery. To this end, data received from the data storage unit 110 may be used for training the artificial neural networks.

Figure 13:
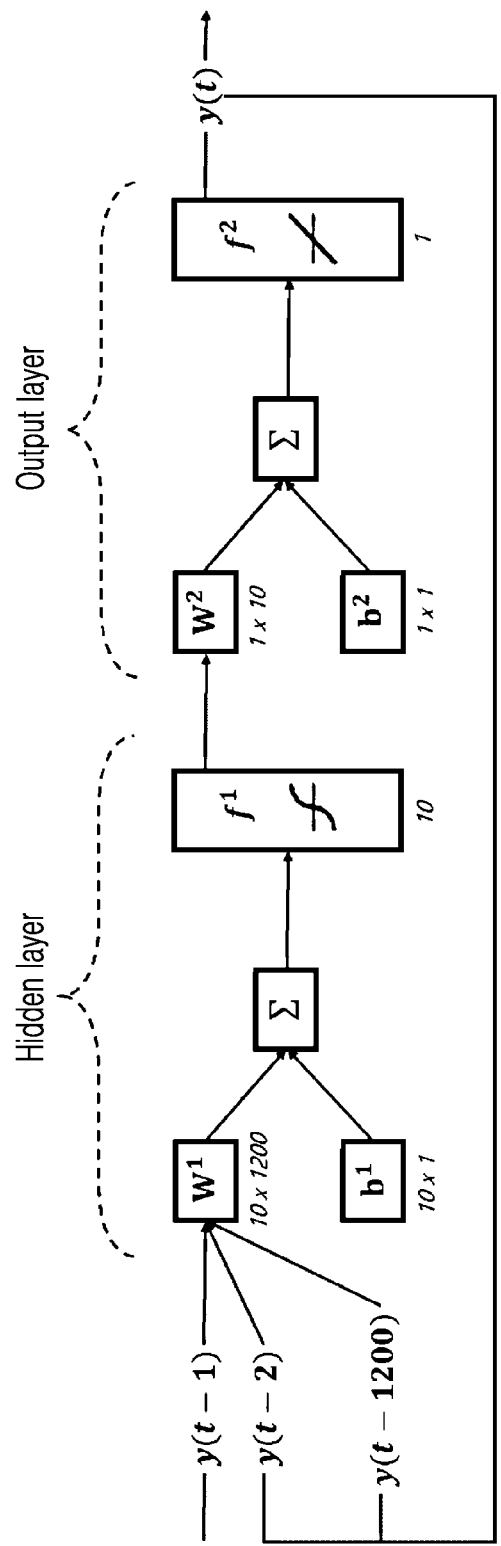
FIG. 13 is a view illustrating a structure of a recurrent neural network according to an embodiment of the present disclosure.

Referring to FIG. 13, according to an embodiment, an artificial neural network for data recovery may be configured using a Nonlinear Auto Regression Neural Network (NAR-Net) which is a type of recurrent neural network. However, it should be noted that the present disclosure is not limited thereto. According to an embodiment, the artificial neural network for data recovery may recover all input data as 1024 data points regardless of magnetic field strength. (3.0 T-based sampling time: 2.048 sec, 9.4 T-based sampling time: 0.8196 sec)

Figure 14:
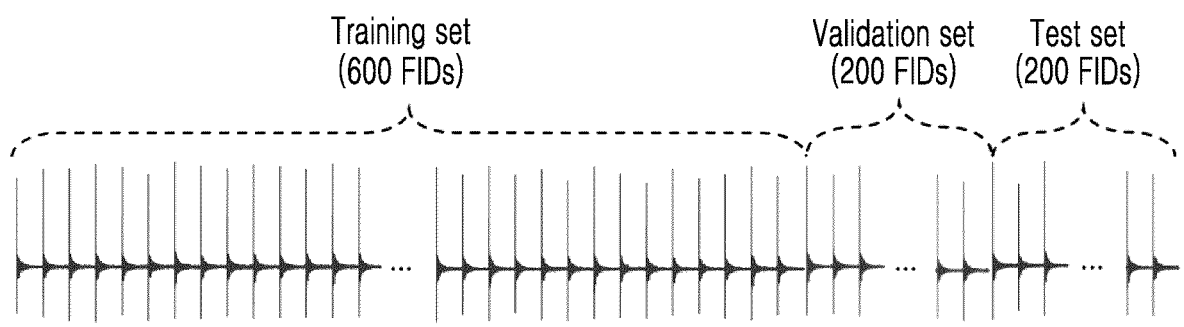
FIG. 14 is a view illustrating a configuration of MRS data used for training a recurrent neural network according to an embodiment of the present disclosure.

Referring to FIG. 14, according to an embodiment, the data recovery unit 130 may truncate data (1024 data points, FID format data) received from the data storage unit 110 by 50 data points from the front of FID (FID-truncation, 3 T, 5% of acquisition time based on 3 T and 9.4 T, the same meaning as incompletely acquired data), and may sequentially connect many pieces of data. (For example, 1000 pieces of FID format data) Each individual piece of data may be sequentially input according to data points into the artificial neural network for signal recovery, and predicted values for the truncated parts may be output.

The accuracy of prediction of the artificial neural network may be evaluated based on cost values (for example, mean square error (MSE) values) obtained by comparison of the output values with corresponding data points (ground truth) before the truncation, and trainable variables such as weights and biases of a hidden layer and an output layer of the artificial neural network may be optimized to minimize the cost values.

Figure 15:
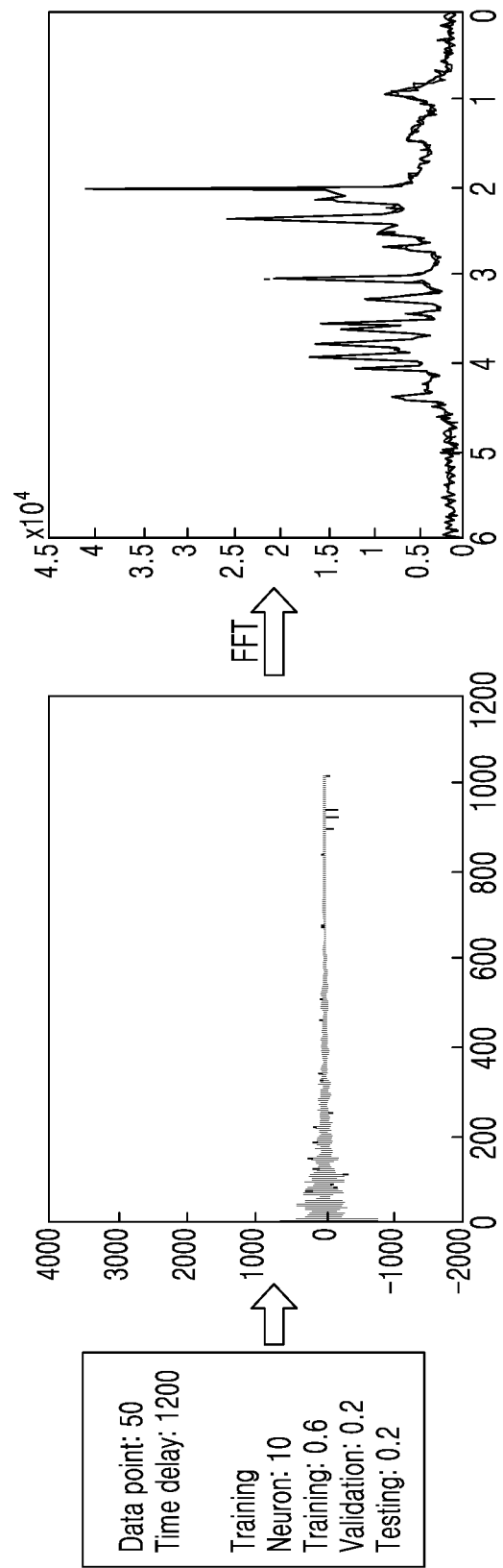
FIG. 15 is a view illustrating results of data recovery by a trained recurrent neural network, according to an embodiment of the present disclosure.

In addition, as shown in the drawing, evaluation may be performed for each epoch and iteration by setting a validation set and a test set to prevent overfitting in training of the artificial neural network. The whole training process of the artificial neural network may be repeatedly performed to validate the reproducibility of the prediction of the artificial neural network. FIG. 15 shows results which are obtained by predicting and recovering truncated FID data in a test data set by using the artificial neural network trained as described above, and results of FFT.

Thereafter, the trained artificial neural network is frozen to prevent training with additionally input data, and then biological data may be recovered. For example, the data recovery unit 130 of the present embodiment may obtain data (four pieces) on normal rat brain tissue and data (six pieces) on rat brain tumor tissue by using a 9.4 T magnetic resonator, perform FID-truncation on the data (truncation by front 50 data points), recover the truncated data, and may evaluate the recovery performance of the artificial neural network based on the difference between the recovered data and the original data. FIG. 16 is an example view illustrating original data obtained from a rat with a brain tumor lesion and data recovered after FID-truncation, and FIG. 17 is an example view illustrating original data obtained from a normal rat and data recovered after FID-truncation.

Hereinafter, an example method of acquiring biological data will be described. First, an animal model is exposed to air in which isoflurane is diluted with oxygen at a concentration of 5% to induce respiratory anesthesia, and in a state in which the anesthesia is maintained with a concentration of 1.5%, the animal model is placed inside a magnetic resonator. Anatomical images may be obtained by triaxial T2-weighted fast spin echo imaging. (TR/TE=3000/30 ms, ETL=4, FOV=40×40 mm2, matrix size=192×192, number of slices=15 (no gap), slice thickness=2 mm, NSA=2). Then, after placing a voxel for acquiring MRS data in a brain tumor site or a contralateral normal site, the linewidth of a water signal is adjusted by performing first-order and second-order auto-shimming and manual-shimming with respect to the voxel. (Reference linewidth: 10 to 20 Hz) MRS data is acquired by a SPECIAL pulse sequence. (TR/TE=4000/3.45 ms, SW=5 kHz, NSA=384, voxel size=9 to 25 mm3, number of data points=2048, zero-filled to 4096).

FIG. 16 shows an original signal of data obtained from a normal brain region, a signal recovered from a truncated signal, results of the difference between the original signal and the recovered signal, and results of FFT performed thereon.

FIG. 17 shows an original signal of data obtained from a brain tumor site, a signal recovered from a truncated signal, results of the difference between the original signal and the recovered signal, and results of FFT performed thereon. In this case, the mean±standard deviation of determination coefficient ($R2$) values between 10 recovered biological data pieces and the original data pieces is obtained as 0.722±0.157. As other evaluation indexes, the mean±standard deviation of mean absolute error (MAE) is 4.484±1.250, and the mean±standard deviation of normalized mean square error (NMSE) is 6.173±1.742.

In a preferred embodiment of the present disclosure, the data recovery unit 130 may produce a signal similar to an original signal by recovering incomplete data obtained in a very short time of about 5% of a general measurement acquisition time. In addition, when a metabolite signal is obtained from an organ with an extremely short acquisition time such as a heart tissue region in which continuous muscle movement occurs by involuntary muscle, the date recovery unit 130 may recover the metabolite signal as a signal processible in the following processes.

Figure 18:
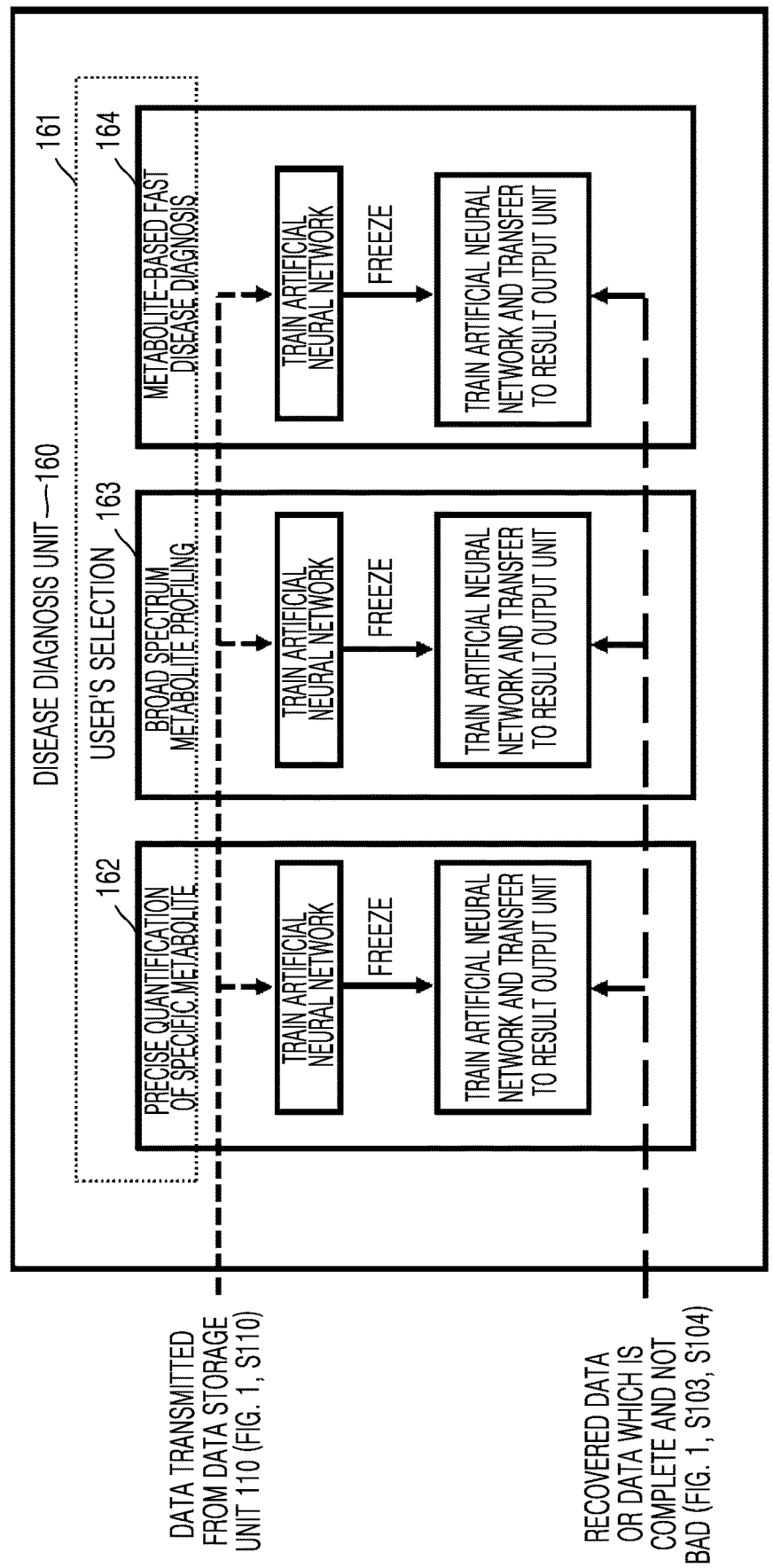
FIG. 18 is a view illustrating an operation of a disease diagnosis unit for diagnosing a disease based on metabolite-based quantitative diagnosis.
Figure 19A:
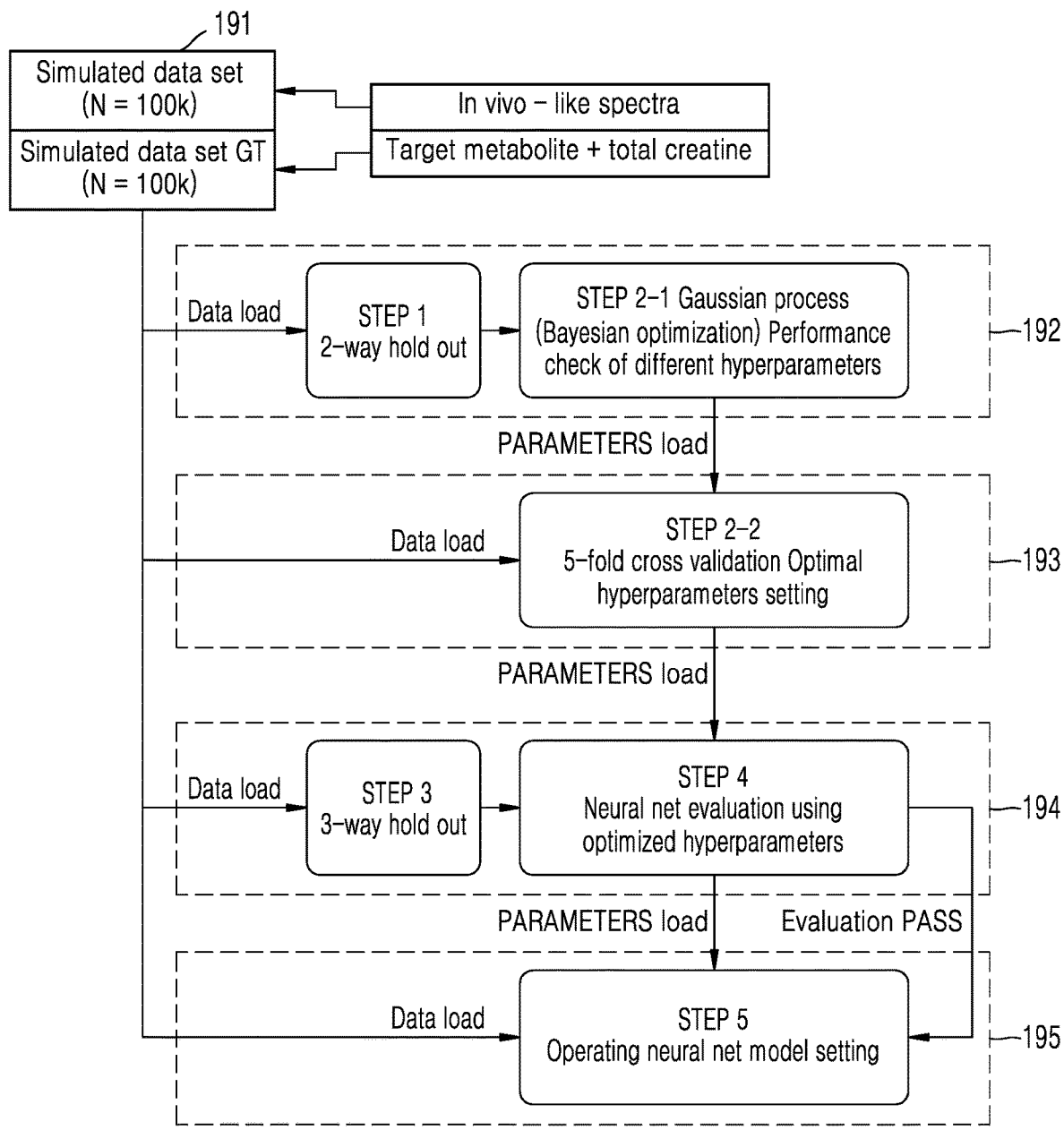
FIGS. 19A-19E illustrate a configuration of a convolutional neural network and an overall training flow therefor, according to an embodiment of the present disclosure.
Figure 19B:
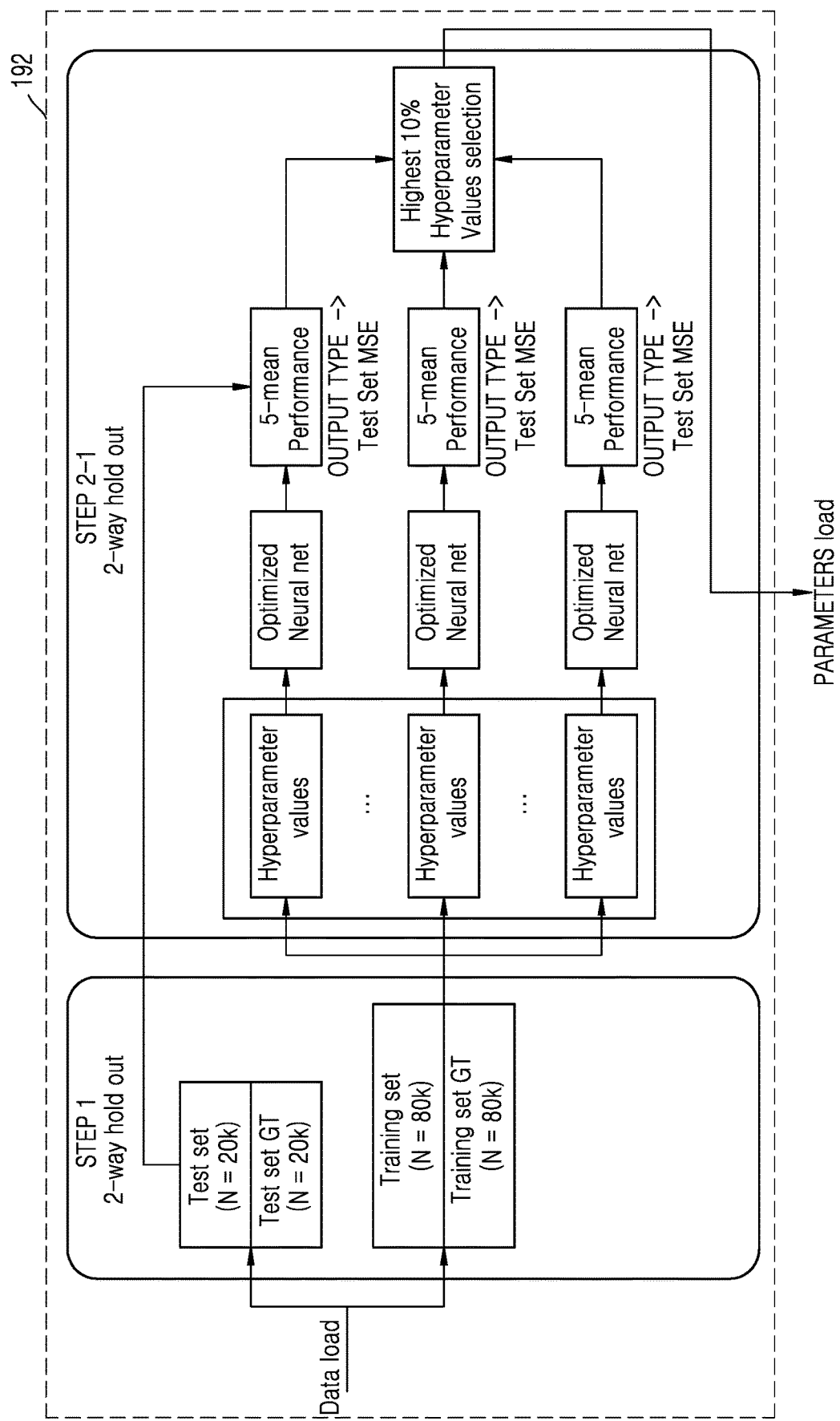
Figure 19C:
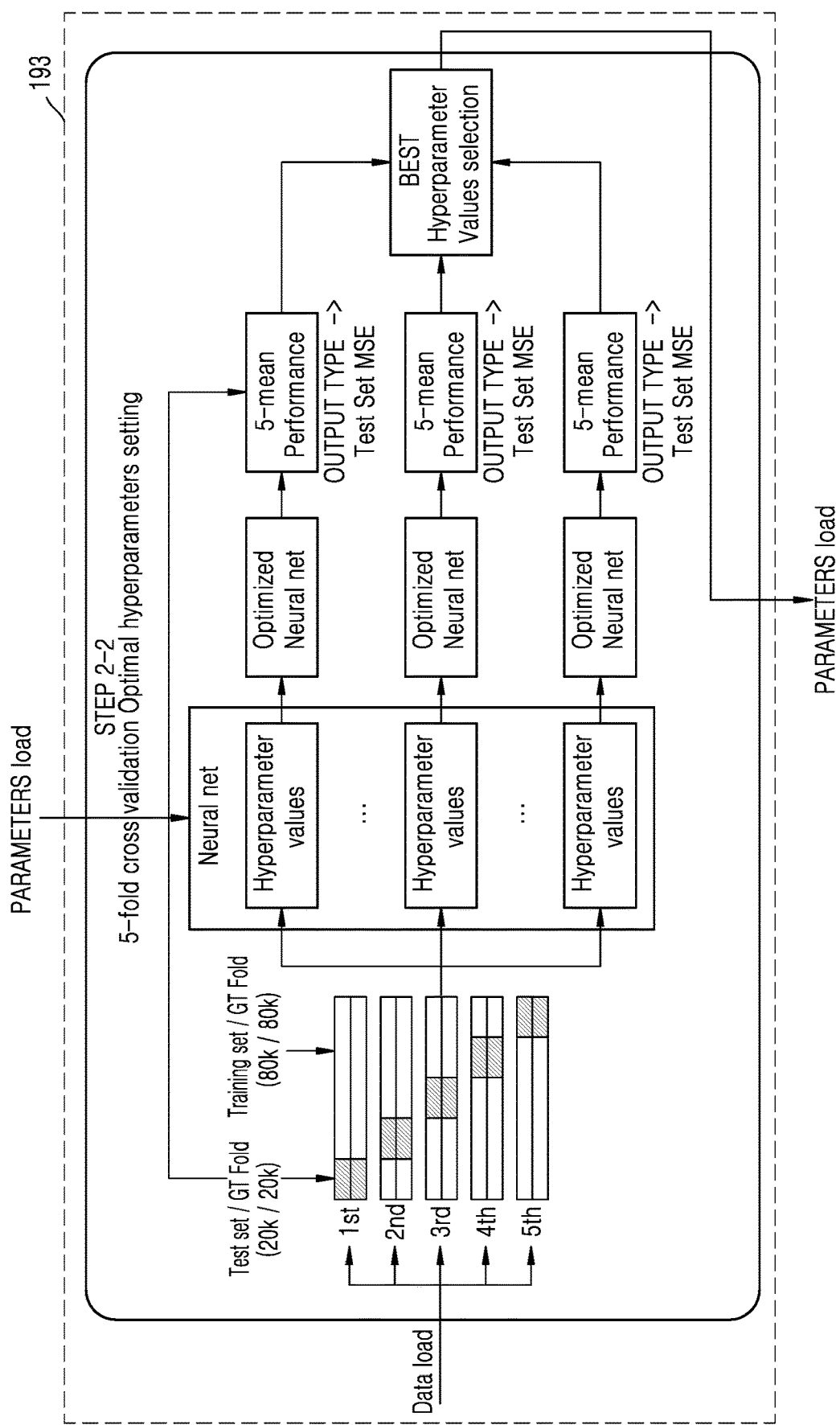
Figure 19D:
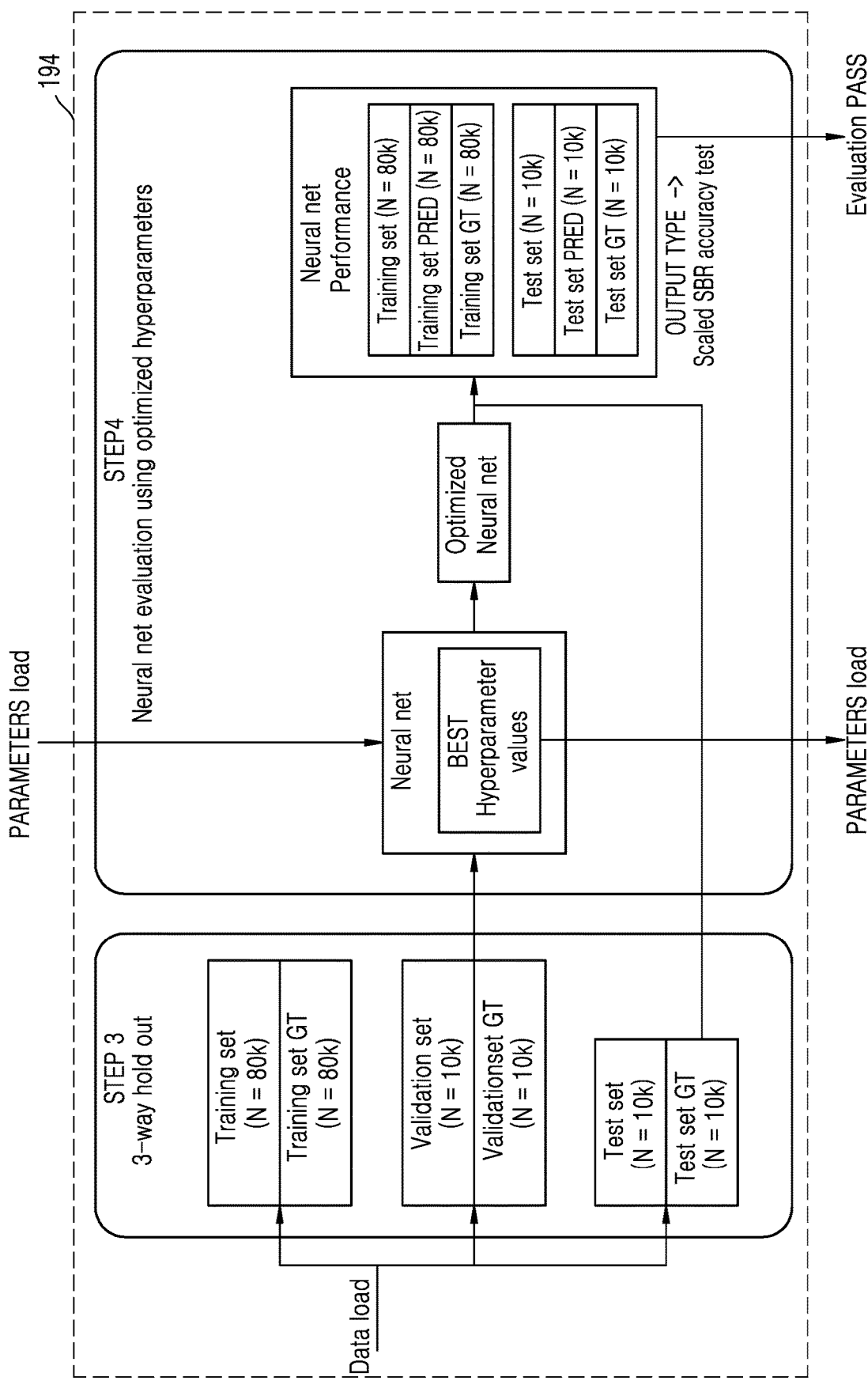
Figure 19E:
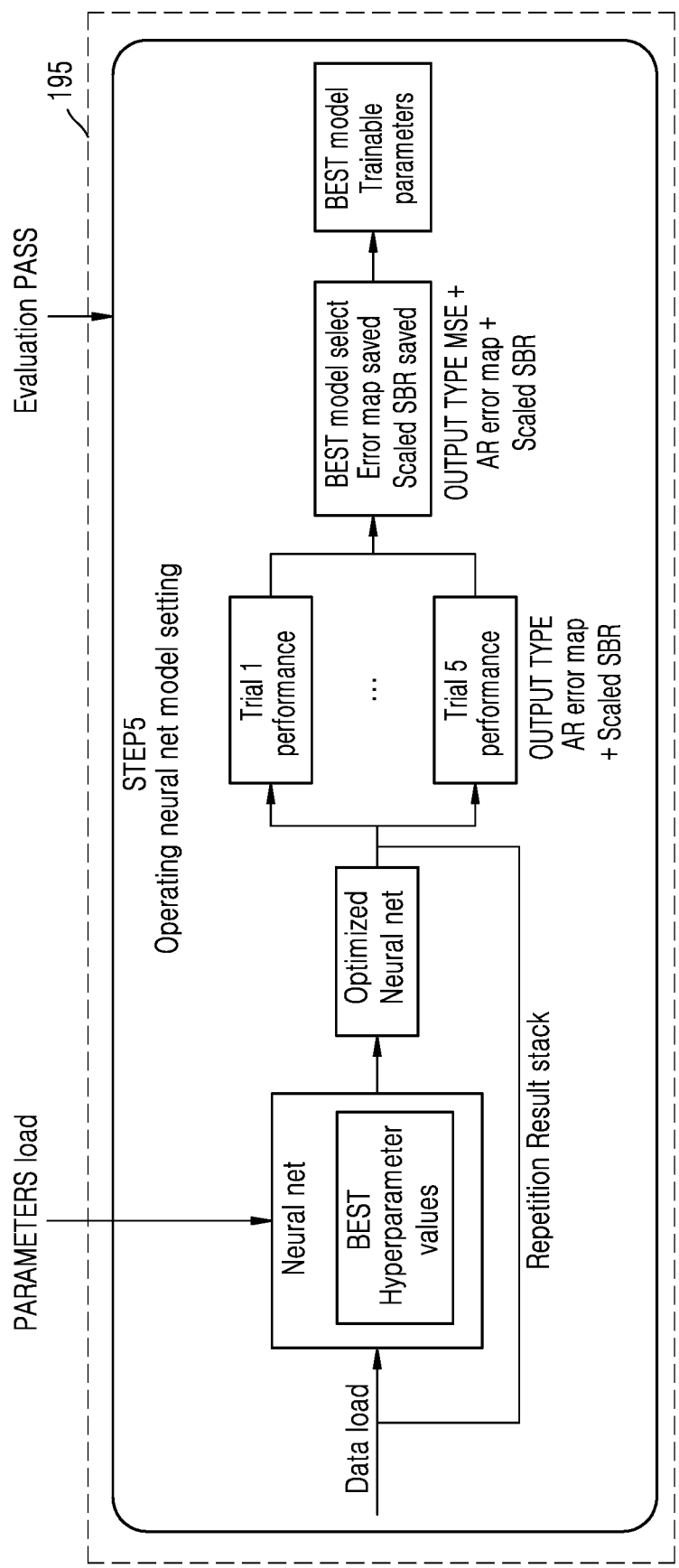

FIG. 18 is a view illustrating an operation of a disease diagnosis unit which diagnoses diseases based on metabolite-based quantitative diagnosis. A description will now be given with reference to FIG. 1.

The disease diagnosis unit 160 (refer to FIG. 1) receives data S110 transmitted from the data storage unit, ground truth data S103 transmitted from the data input unit 120, and recovered incomplete/bad data S104. The disease diagnosis unit 160 (refer to FIG. 1) trains an artificial neural network by using the data S110 transmitted from the data storage unit. According to user's selection, the artificial neural network may be trained for precise quantification 162 of a specific metabolite, broad spectrum metabolite profiling 163, or metabolite-based fast disease diagnosis 164. To this end, a selection interface 161 may be provided to a user.

In a preferred embodiment of the present disclosure, the artificial neural network in the disease diagnosis unit 160 may be generated based on a convolutional neural network (CNN). A method of training an artificial neural network will be described in detail with reference to FIGS. 19 and 20.

Figure 20:
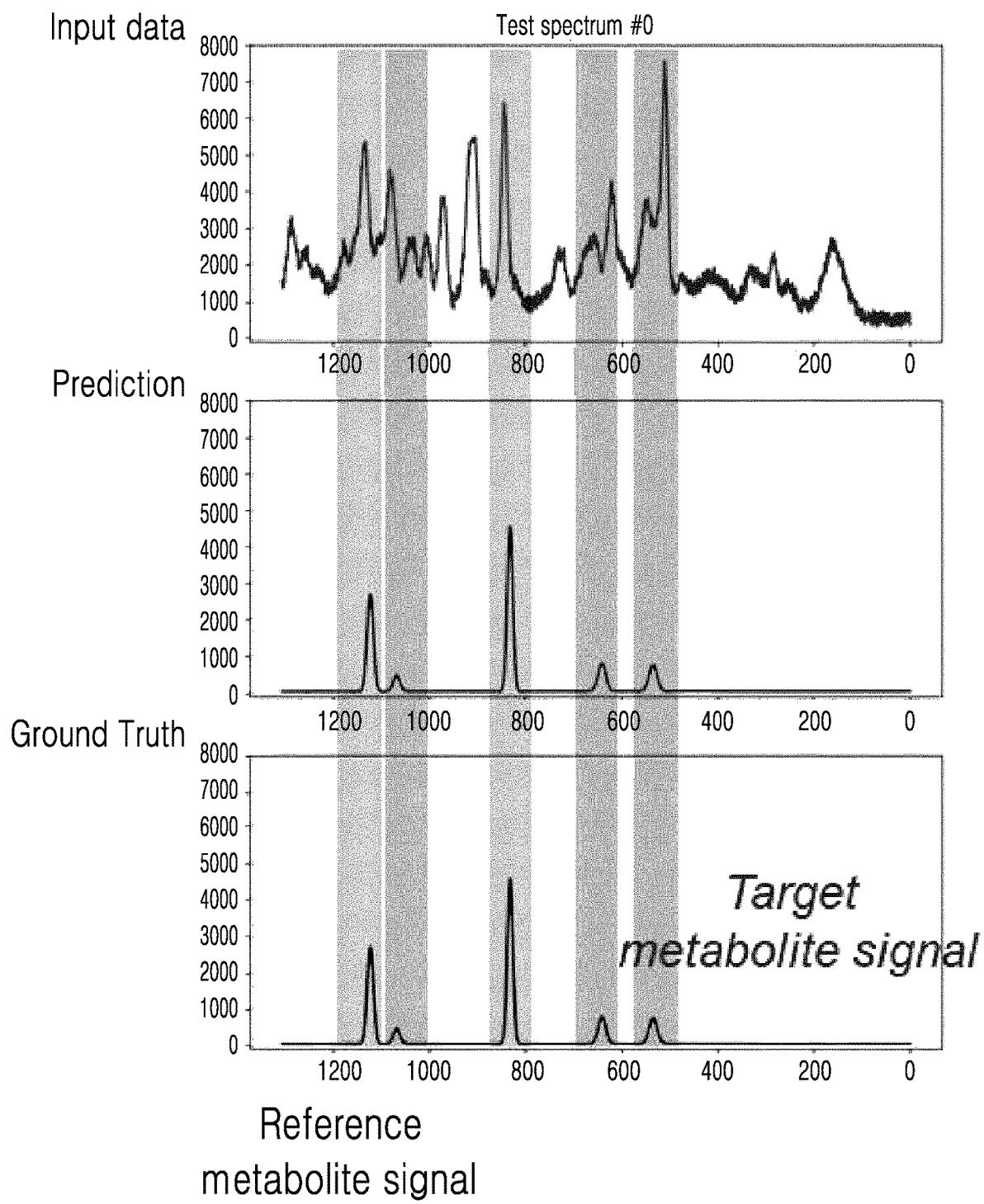
FIG. 20 is a view illustrating original data to be predicted by a convolutional neural network, predicted data (spectral editing), and ground truth data, according to an embodiment of the present disclosure.

Reference numerals 191, 192, 193, 194 and 195 in FIG. 19 illustrate a process of training an artificial neural network for precise quantification of a specific metabolite based on a CNN. In addition, FIG. 20 shows example result data output through the artificial neural network used in the embodiment shown in FIG. 19. The artificial neural network for precise quantification of a specific metabolite may include a total of 32 layers, which are designed in the order of input layer—hidden layer—output layer. The hidden layer may include: a convolutional block having nine convolutional layers—a batch normalization layer—an activation (relu) layer; two fully connected layers; and a regression layer. Steps for training an artificial neural network for precise quantification of a specific metabolite is as follows.

The disease diagnosis unit 160 may acquire 100,000 pieces of data and ground truth data corresponding thereto from the data storage unit 110. The above-described data is used for training the artificial neural network, and ground truth data include a signal pair of a specific metabolite and a reference metabolite (for the purpose of expressing relative concentrations). The number of target metabolites is 15 (excluding Cr and PCr which are reference metabolites). The training process in this form is referred to as a signal editing process.

Thereafter, the disease diagnosis unit 160 performs Bayesian optimization in two steps of coarse searching and fine searching to set hyperparameters of the artificial neural network. In this case, the hyperparameters which are searched for in Bayesian optimization are the number and size of convolutional filters included in each layer, the number of neurons that are fully connected, and an initial learning speed ratio.

Thereafter, the disease diagnosis unit 160 may perform a final evaluation on artificial neural networks configured by top ten hyperparameter combinations which are selected through the Bayesian optimization.

The evaluation may be performed through 5-fold cross validation, and the disease diagnosis unit 160 may select a hyperparameter combination showing intermediate performance among them. The disease diagnosis unit 160 including an artificial neural network having the hyperparameter combination determined in the above-mentioned steps may perform training by dividing fetched data into data for training (80%)/data for validation (10%)/data for test (10%).

The disease diagnosis unit 160 of the present embodiment may use results obtained through a test data set as evaluation factors for a trained artificial neural network. In this case, the disease diagnosis unit 160 constructs an operating model which is frozen for artificial neural network prediction.

In addition, the disease diagnosis unit 160 may repeat the above-mentioned procedures to form operating models different from each other according to the types of specific metabolites included in ground truth data.

Hereinafter, a method of performing prediction and evaluation using the artificial neural network for precise quantification of a specific metabolite described above with reference to FIG. 18 will be described in detail with reference to FIGS. 21 to 23.

Figure 22:
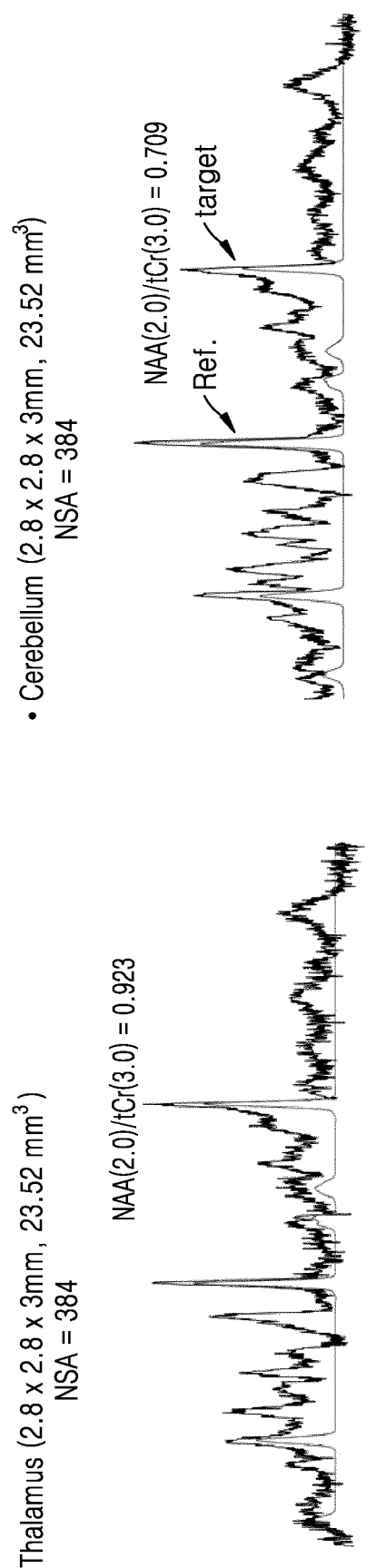
FIG. 22 is a view illustrating original data obtained from each part of a normal rat and NAA metabolite spectral editing prediction results, according to an embodiment of the present disclosure.
Figure 23:
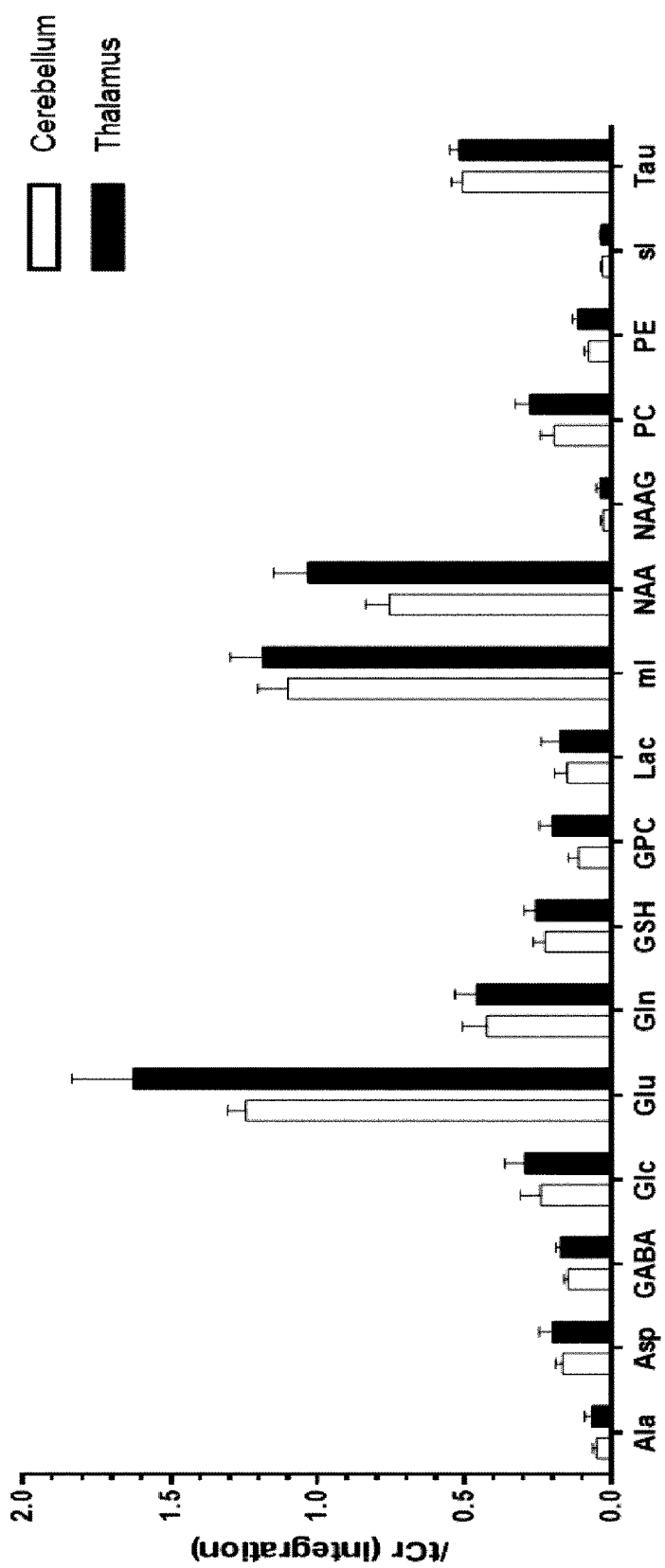
FIG. 23 is a view illustrating a mean and standard deviation graph for metabolites at different sites (14 normal rats), and P-values as t-test results, according to an embodiment of the present disclosure.

FIG. 21 is a view illustrating MAE for each metabolite which is obtained from 10,000 test data sets, FIG. 22 is a view illustrating original data obtained from each part of a normal rat and NAA metabolite spectral editing prediction results, and FIG. 23 is a view illustrating a mean and standard deviation graph for metabolites at different sites (14 normal rats), and P-values as t-test results.

An artificial neural network configured for each metabolite may be evaluated by the disease diagnosis unit 160 using test data sets used in training and data obtained with a 9.4 T magnetic resonator from two different regions of a normal rat brain.

In this case, the mean absolute error (MAE) of predicted results of 10,000 test data sets with respect to ground truth is shown for each metabolite in FIG. 21. It is shown that the mean absolute error (MAE) is equal to or less than 20% or 10% for each metabolite although the data are not used for training an artificial neural network.

It is assumed that specific biological data are obtained from 14 rats in the following manner. First, an animal model is exposed to air in which isoflurane is diluted with oxygen at a concentration of 5% to induce respiratory anesthesia, and is then placed in a magnetic resonator while maintaining the anesthesia by exposing the animal model to air diluted to a concentration of 1.5%.

Anatomical images may be obtained by triaxial T2-weighted fast spin-echo imaging. (TR/TE=3000/30 ms, ETL=4, FOV=40×40 mm2, matrix size=256×256, number of slices=15 (no gap), slice thickness=2 mm, NSA=2). Then, after placing voxels for acquiring data in the cerebellum and thalamus, the linewidth of water signals is adjusted by performing first-order and second-order auto-shimming and manual-shimming with respect to the voxels. (Reference linewidth: 10 to 20 Hz) Data is acquired by a SPECIAL pulse sequence. (TR/TE=4000/3.45 ms, SW=5 kHz, NSA=384, voxel size=23.52 mm3, number of data points=2048, zero-filled to 4096).

FIG. 22 shows an original signal obtained from each brain region, and a metabolite prediction spectrum based on the data. FIG. 22 shows only NAA. In this case, mean values and deviations of data obtained from each region of the brain, and results of a paired t-test thereon showing that P-value<0.05 as a result of a paired t-test thereon are shown in FIG. 23. From this, it is confirmed that the disease diagnosis unit 160 performs automatic quantification of specific metabolites through signal editing with high accuracy according to a preferred embodiment of the present disclosure.

In a preferred embodiment of the present disclosure, the disease diagnosis unit 160 may include an artificial neural network for complex metabolite profiling as well as an artificial neural network for precise quantification of specific metabolites.

Figure 24:
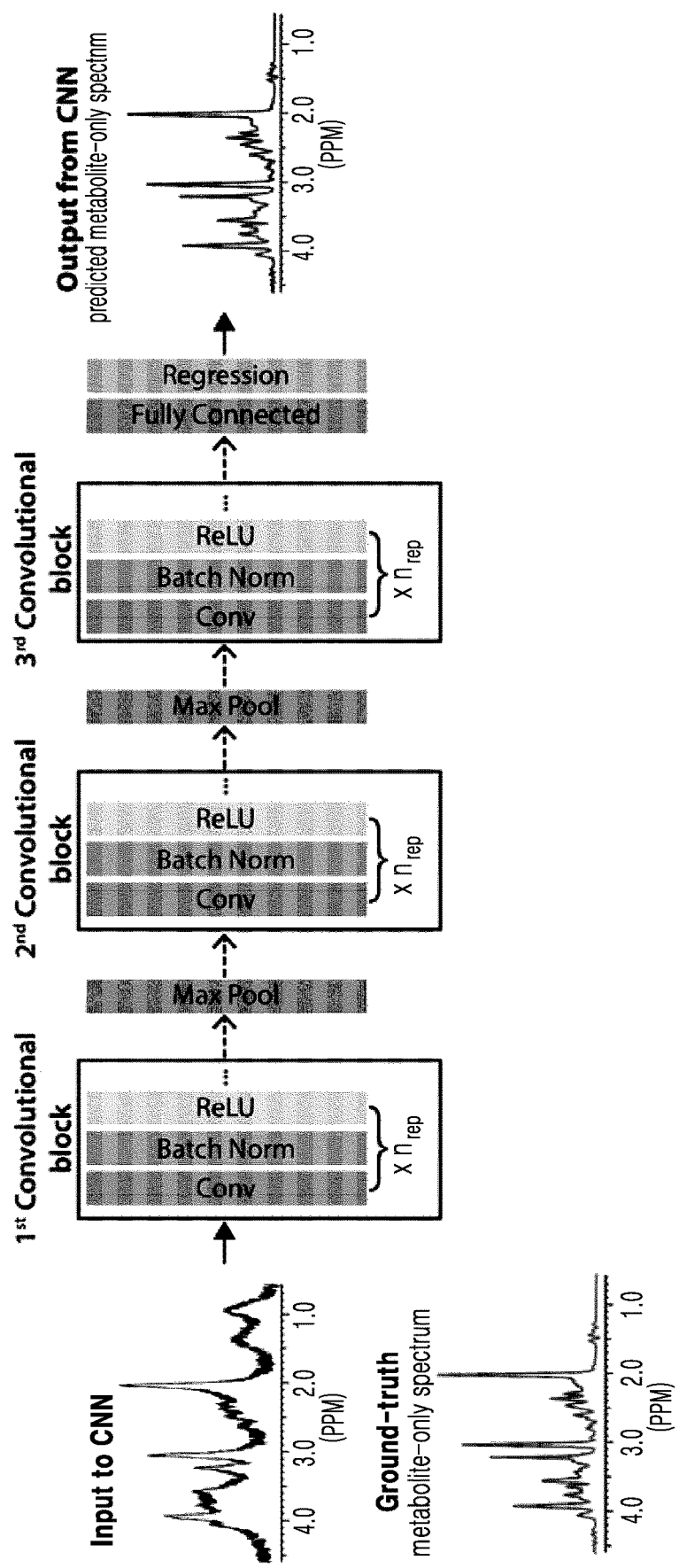
FIG. 24 is a view illustrating a configuration of a corresponding convolutional artificial neural network, overall training processes therefor, and results output from the artificial neural network, according to an embodiment of the present disclosure.

Hereinafter, a method of training an artificial neural network which is included in the disease diagnosis unit 160 for complex metabolite profiling will be described in detail with reference to FIG. 24 according to an embodiment of the present disclosure.

Data received from the data storage unit data storage unit 110 may be used for training an artificial neural network training for complex metabolite profiling according to an embodiment. The artificial neural network for complex metabolite profiling may have an artificial neural network configuration based on a convolutional neural network (CNN).

According to an embodiment, the artificial neural network for complex metabolite profiling may include a total of 41 layers, which are designed in the order of input layer—hidden layer—output layer. In this case, the hidden layer may include: a convolutional block having three convolutional layers—a batch normalization layer—an activation layer (Relu layer); one fully connected layer; and a regression layer. According to an embodiment, the convolutional block may determine the number of repetitive insertions by Bayesian optimization (described later). In some embodiments of the present disclosure, the artificial neural network for complex metabolite profiling may perform an optimization process (described below) for profiling a wide range of metabolites.

First, the disease diagnosis unit 160 may retrieve 50,000 pieces of data and corresponding ground truth data from the data storage unit 110. The 50,000 pieces of data is used for training the artificial neural network, and the ground truth data may include metabolite signals which are linearly combined under high quality conditions (line-narrowed, frequency adjusted, phase adjusted). A total of 17 types of target metabolites may be included. Hereinafter, the training process in this form will be referred to as an intrinsic metabolite signal mining process.

The disease diagnosis unit 160 may perform Bayesian optimization to set hyperparameters of the artificial neural network. In this case, the hyperparameters searched for in Bayesian optimization may be the number of iterations of each convolution block, the number and size of convolution filters included in the convolution block, the number of fully connected neurons, and an initial learning speed ratio. The artificial neural network including a combination of hyperparameters selected through Bayesian optimization is trained by dividing fetched data into data for training (80%)/data for validation (10%)/data for test (10%). In this case, results obtained using a test data set may be used as evaluation factors for the trained artificial neural network. Then, the disease diagnosis unit 160 may construct an operating model which is in a frozen state for use in prediction using the artificial neural network. In addition, the disease diagnosis unit 160 may perform 10-cross validation to verify the reproducibility of the constructed operating model.

A prediction and evaluation method using an artificial neural network for complex metabolite profiling included in the disease diagnosis unit 160 will be described in detail with reference to FIGS. 25 to 28 according to an embodiment.

In an embodiment, the evaluation of an artificial neural network for complex metabolite profiling may be performed using 5,000 test data sets which are used for training and normal group brain data which is obtained from a 3.0 T magnetic resonator. Hereinafter, a method of obtaining a metabolite concentration from data predicted using an artificial neural network for complex metabolite profiling will be described in detail.

In the present embodiment, the disease diagnosis unit 160 may use a Moore-Penrose pseudoinverse matrix to calculate the multiplication coefficient value of each metabolite signal from data predicted by an artificial neural network for complex metabolite profiling. The calculated multiplication coefficient value refers to the intrinsic concentration of each metabolite, and the disease diagnosis unit 160 of the embodiment may calculate an absolute error between the value and the intrinsic concentration value stored together with ground-truth data. In this case, the mean absolute error of all data may be expressed as a mean absolute percent error (MAPE, %).

Figure 25:
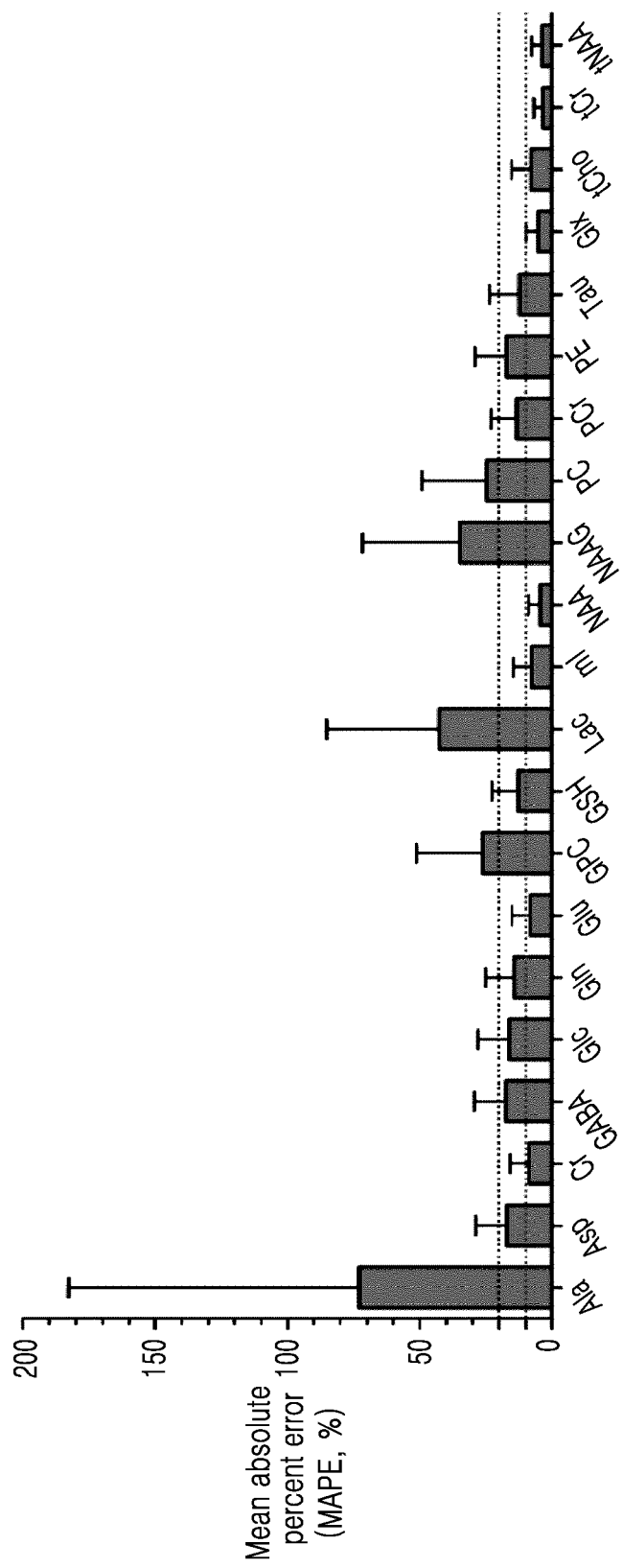
FIG. 25 is a view illustrating MAPE values for 5,000 test sets, according to an embodiment of the present disclosure.

FIG. 25 shows MAPE values of 5000 test data sets together with a 10% baseline and a 20% baseline.

Referring to the drawing, although the data has not been used for training, most metabolites have an MAPE value of 20% or less, and major metabolites have an MAPE value of 10% or less. Hereinafter, a method of acquiring biological data will be described according to an embodiment of the present disclosure.

First, after placing the subject in a magnetic resonator, anatomical images may be obtained by triaxial T2-weighted fast spin-echo imaging. (TR/TE=2000/25 ms, ETL=8, FOV=250×250 mm2, matrix size=256×256, number of slices=15 (no gap), slice thickness=8 mm, NSA=2). Thereafter, after placing a voxel for acquiring MRS data in the left frontal lobe in which white matter is mainly distributed, auto-shimming is performed with respect to the voxel to adjust the linewidth of a water signal. (Reference linewidth: 10 to 15 Hz) In addition, MRS data may be acquired with a PRESS pulse sequence. (TR/TE=2000/30 ms, spectral bandwidth (SW)=2 kHz, NSA=64 (NSA 8×8), voxel size=8 cm3, number of data points=2048, zero-filled to 4096)

Figure 26A:
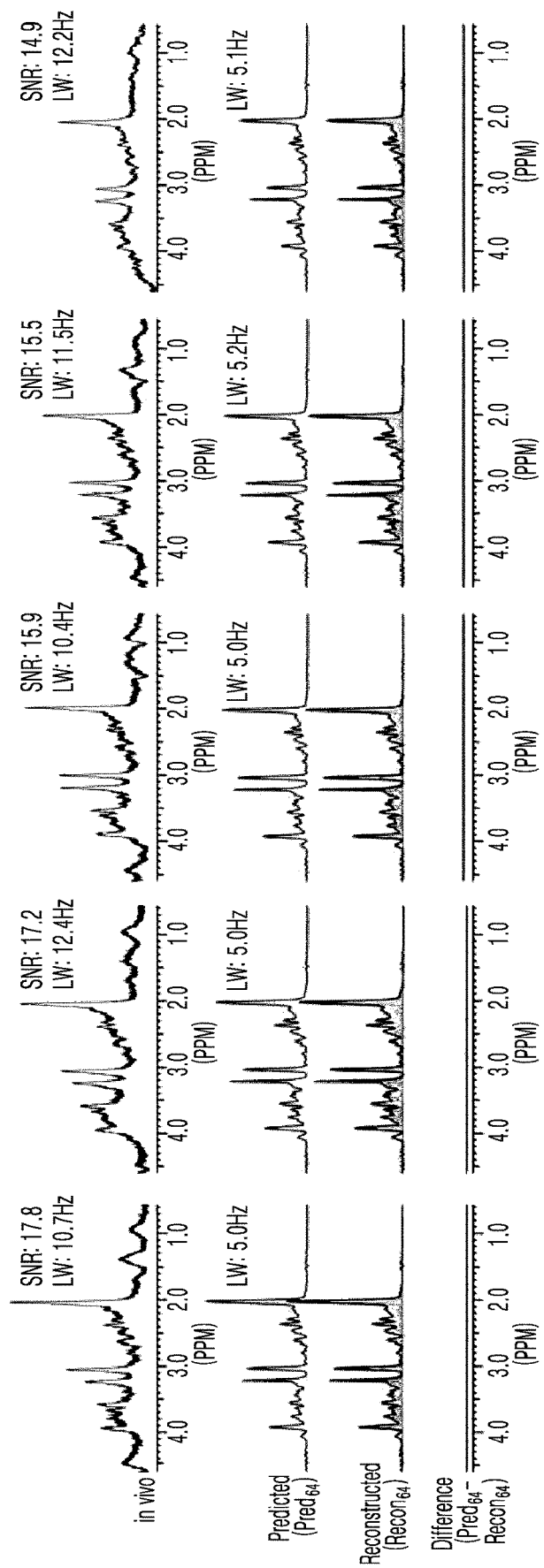
FIGS. 26A-26C illustrate biological data obtained from a group of five normal persons and results of prediction by an artificial neural network, according to an embodiment of the present disclosure.
Figure 26B:
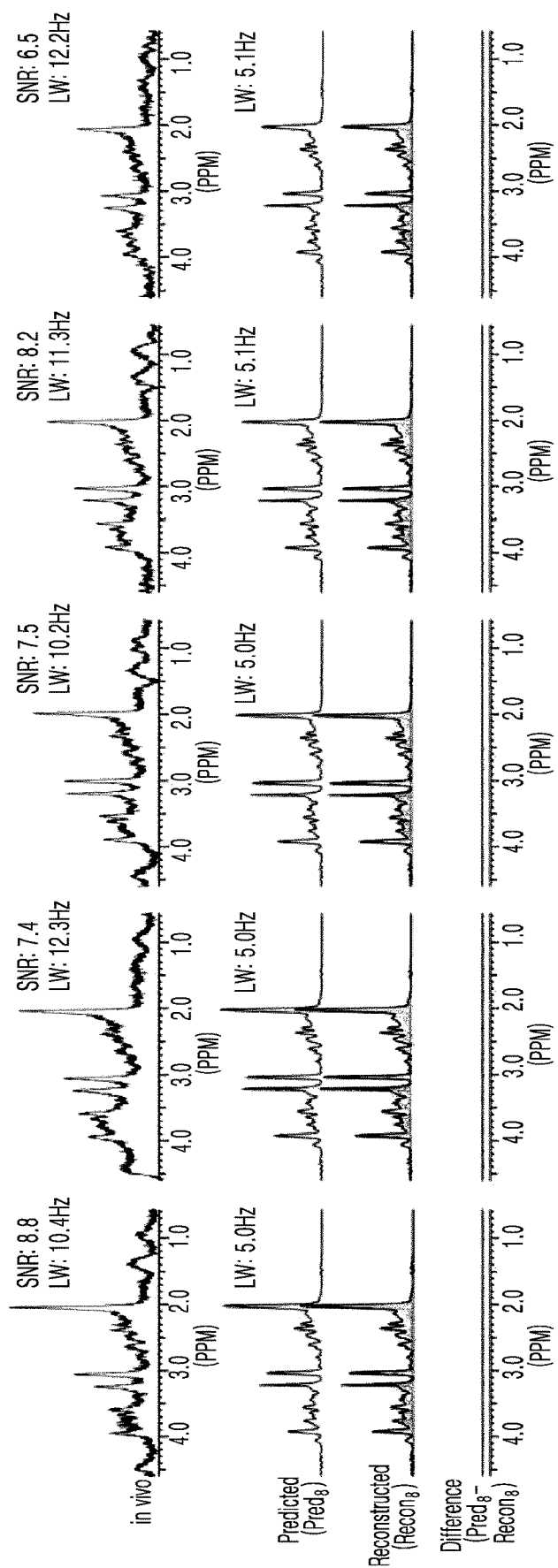
Figure 26C:
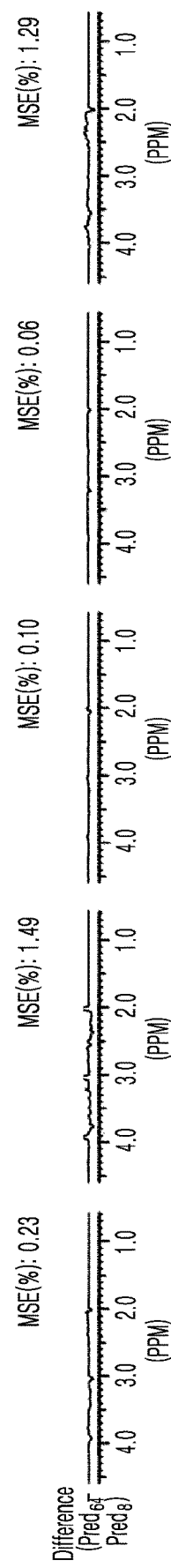

FIG. 26 is a view illustrating NSA 64(a), NSA 8(b) data in vivo of 5 normal groups which are predicted by an artificial neural network, and individual signals (Recon) of metabolites which are predicted by a Moore-Penrose pseudoinverse matrix, and the difference from signals predicted by the artificial neural network. In addition, the difference (c) between signals of the NSA 64 data and the NSA 8 data which are predicted by the artificial neural network are shown.

FIG. 27 is a view illustrating results of metabolite-specific quantification for NSA 64 data of a normal group of five persons, in which results obtained from data of each person by using an artificial neural network are compared with LCModel which is most commonly used as an NLLS fitting method. In addition, the range of the concentration of each metabolite which is known through previous studies is shown (dash lines refer to mean values).

FIG. 28 shows variations in the absolute percentage difference (%) of results of quantification of each metabolite obtained from NSA 8-NSA 56 data with respect to results of quantification obtained from NSA 64 data, in mean value of result values of five persons. FIG. 28 shows result values obtained using an artificial neural network, result values obtained using an LC Model, and mean CRLB (%) of five persons expressed as a reliability scale value for results of quantification with LCModel.

The main reasons for the technical limitations of conventional MRS in non-invasive quantitative analysis of brain metabolites are limited scan times, low SNR in the spectrum caused by basically low metabolite concentrations, and baseline signals which are not clearly defined and overlap metabolite signals throughout the whole spectrum. However, in quantification processes using the artificial neural network included in the disease diagnosis unit 160 according to some embodiments of the present disclosure, metabolites may be quantified with a low error rate by improving SNR and effectively removing baseline signals. Some embodiments of the present disclosure show the possibility of developing new data processing techniques based on artificial neural networks to overcome the limitations of the existing MRS, and clearly show the possibility of developing techniques for significantly reducing the time of clinical scanning particularly based on artificial neural networks having high performance in improving signal quality, thereby making it possible to quantify metabolites using a proper artificial neural network selected according to the purposes of users and situations.

In a preferred embodiment of the present disclosure, as shown in FIG. 18, the disease diagnosis unit 160 may include an artificial neural network for performing rapid disease diagnosis 164 (refer to FIG. 18) based on a metabolite signal pattern.

Figure 29:
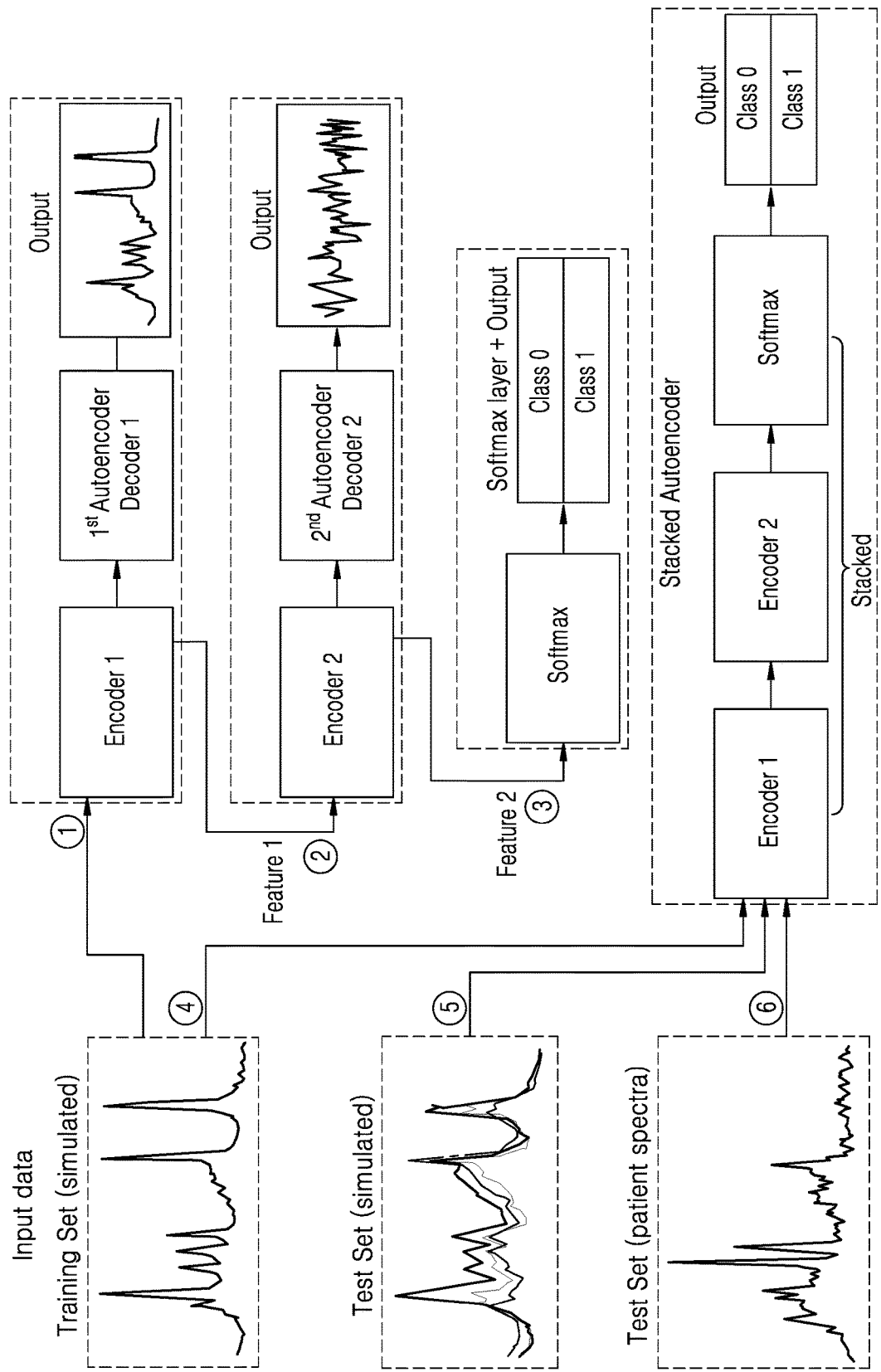
FIG. 29 is a view illustrating a configuration of an artificial neural network for fast disease diagnosis, a training process, and a prediction process, according to an embodiment of the present disclosure.

FIG. 29 shows a configuration of the above-described artificial neural network using a stacked autoencoder, overall training processes, and results output from the artificial neural network.

A training unit of the artificial neural network that performs signal pattern-based fast disease diagnosis may include: two training layers each having an encoder-decoder form; and a softmax layer configured to perform diagnostic classification according to the overall patterns of metabolite signals. After training, the neural network may include two encoder layers and one softmax layer. The artificial neural network of the embodiment may set, as a target metabolite, 2-hydroxyglutarate (2HG) which is known to accumulate as a result of isocitrate dehydrogenease (IDH) mutation in a lesion of a brain tumor patient, and may perform classification into an IDH-wild type (not including a 2HG signal in an MRS signal) or an IDH-mutant type (including a 2HG signal in an MRS signal) depending on the presence of the target metabolite and changes in various metabolites related to mutation.

Hereinafter, a method of training an artificial neural network for performing fast disease diagnosis based on a metabolite signal pattern will be described in detail. In an embodiment, the disease diagnosis unit 160 may acquire 1.5 million pieces of data and ground truth data corresponding thereto from the data storage unit 110. The pieces of data may include: 750,000 brain tumor mimic MRS data including 2HG metabolite signals and other metabolites having various concentration ratios; and brain tumor mimic MRS data including no 2HG metabolite signal. In an embodiment, the pieces of data may be used for training the artificial neural network, and the ground truth data may include actual concentration values and gene types of 2HG metabolites. In an embodiment, acquired data may be divided into training data and test data and may then be used. Results obtained using test data sets may be used as evaluation factors for the artificial neural network after training.

Referring to FIG. 30, the evaluation of the trained artificial neural network may be performed using data obtained from thirteen brain cancer patients by using a 3.0 T magnetic resonator. Final results of data predicted through the artificial neural network may be expressed as 2HG-negative (that is, 2HG is not detected) or 2HG-positive (that is, 2HG is detected), and gene type sequencing may be performed on brain cancer tissue obtained from each patient to determine whether the prediction results are accurate. FIG. 30 shows gene types, results of prediction using the artificial neural network, and results of 2HG concentrations quantified using an LC model (2HG-positive in case of concentration detection, and 2HG-negative in case of no concentration detection).

In the embodiment shown in FIG. 30, the accuracy of prediction using the artificial neural network is 77% (accurate 2HG detection/non-detection for 10 people's data out of 13 people's data), and the accuracy of the LC model is 46% (accurate 2HG detection/non-detection for 6 people's data out of 13 people's data). Although one of the most important research and clinical diagnostic topics in the field of MRS is the detection of 2HG metabolite signals accumulated by IDH mutation in the lesions of brain tumor patients, the detection of 2HG is very difficult due to signal overlap between various metabolite signals and signal yield problems caused by low metabolite concentrations. In some embodiments of the present disclosure, the limitations of these existing techniques are overcome by analyzing data of brain tumor patients using the artificial neural network, and thus the rate of diagnosis related to IDH-mutation determination is significantly improved to 77% compared to 46% in the case of using the LCmodel which is a metabolite quantification method using NLLS fitting.

In a preferred embodiment of the present disclosure, the result output unit 190 may output results of quantification or diagnosis based on information received from the artificial neural network training unit 170 and the artificial neural network prediction unit 180 of the disease diagnosis unit 160. Hereinafter, the operation of the result output unit 190 will be described in detail with reference to FIGS. 31 and 32.

Figure 31:
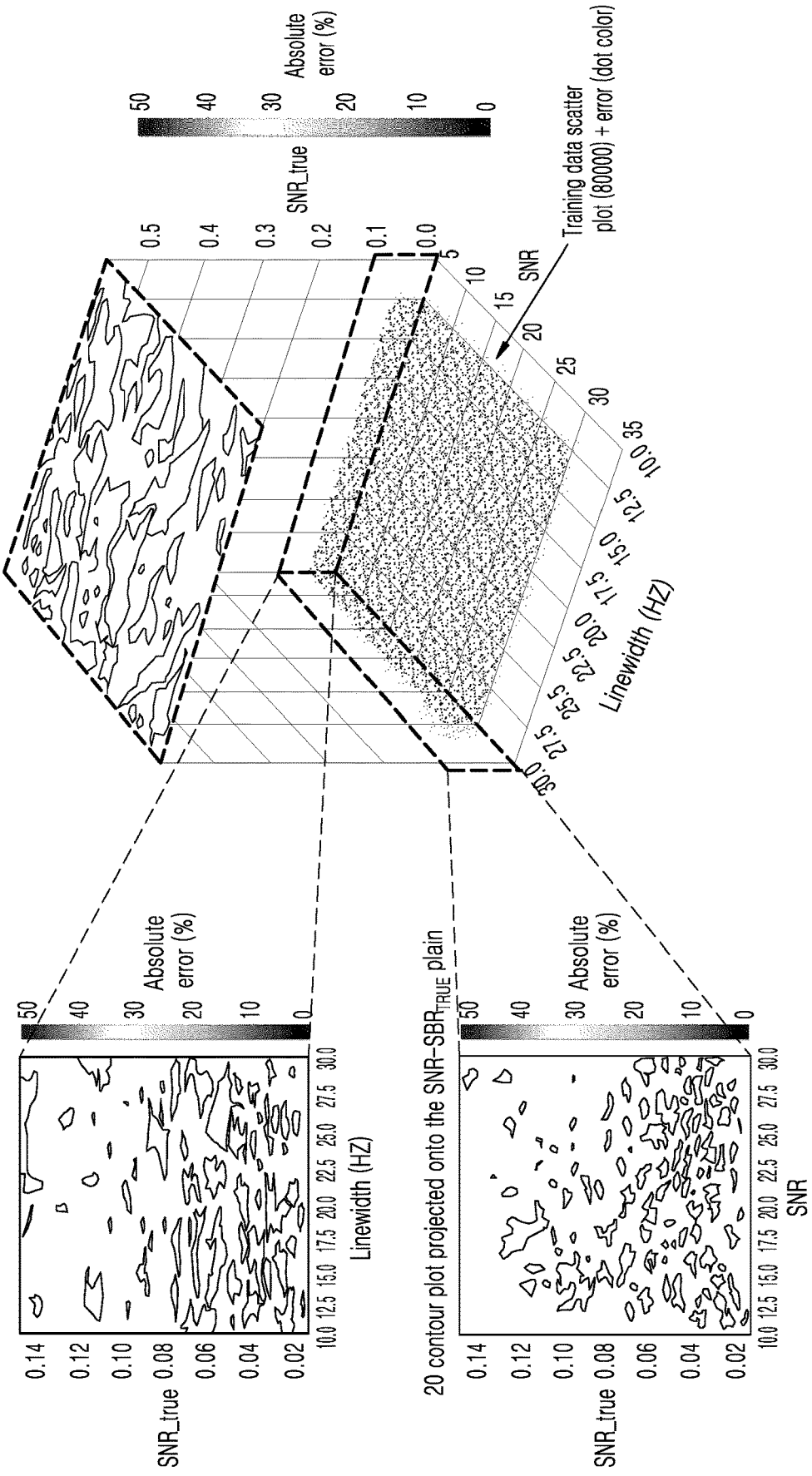
FIG. 31 is a view illustrating a predicted error map for a specific metabolite according to an embodiment of the present disclosure.

FIG. 31 is a map showing errors predicted for a specific metabolite, and FIG. 32 shows errors predicted for results of metabolite quantification performed on data included in a test data set.

The result output unit 190 may obtain, from the data storage unit 110, data used for training each artificial neural network for quantification, data predicted by each of the trained artificial neural networks, and ground truth data corresponding thereto.

Thereafter, the result output unit 190 may calculate LW and SNR, which are factors determining signal quality, from raw data used for training. In addition, the result output unit 190 may calculate the signal-to-background ratio (SBR) of predicted data and original data (SBRPRED).

In addition, the result output unit 190 calculates the SBR of ground truth data and the original data in the same manner (SBRTRUE). In this case, the lower the SBR value, the more difficult it is to quantify corresponding data.

Then, the result output unit 190 may calculate a difference ratio of between results of quantification based on data predicted for original data and results of quantification included in the ground truth data (ARPRED/GT).

In this case, the result output unit 190 may express coordinates related to the quality/quantification difficulty of original data in a triaxial space based on the LW, SNR, and SBRTRUE described in the above, and may express ARPRED/GT for the data by using a color scale.

In addition, the result output unit 190 forms three contour maps by projecting, into two-dimensional space, information on data quality, quantification difficulty, and quantification errors in a three-dimensional space. The height value of each contour map may be expressed as ARPRED/GT in common.

In this case, the result output unit 190 may divide LW, SNR, SBRTRUE at intervals of 0.1, check SBRPRED for predicted data included in each quality factor interval, determine the minimum/maximum ARPRED/GT values presenting at positions where the corresponding values exist in the three-dimensional space, and store them in the form of a matrix.

FIG. 31 is a view illustrating 100,000 pieces of original data used for training an artificial neural network for precisely quantifying a specific metabolite, predicted data corresponding thereto, and representation of quality/quantification difficulty in a triaxial space and on biaxial plane contour maps with respect to the metabolite by using ground truth data.

To verify the algorithm constructed in the present embodiment, as shown in FIG. 32, Gln metabolite quantification is predicted with respect to random data not used for training artificial neural networks (that is, without knowing ground truth), errors of results thereof are calculated (quantification lower/upper limit (%)), and errors are expressed compared to actual true values (actual quantification error). Through this, it is understood that since actual error values (−1.7%)

obtained in some embodiments of the present disclosure are within a predicted error range (−10.4% to 2.6%), the error prediction is meaningful.

In the above-described embodiments of the present disclosure, the same verification as described above is performed using 1,000 nontrained random data shows that actual error values are within a predicted error range for all metabolites at a ratio of 98% (that is, a predicted error reliability) for the total data. In an LCModel used for metabolite quantification, CRLB (%) is used as an indicator of reliability of quantification results. However, the indicator is not for expressing errors between quantification results and actual true values, but is for expressing how precisely a quantification value is recalculated when fitting is repeatedly performed under conditions similar to original signal quality conditions. Therefore, bias may occur when results of quantification are interpreted using the indicator. In the present embodiment, however, errors are predicted with respect to actually expected true values, and thus metabolites may be quantitatively analyzed more accurately than the existing methods.

The apparatus described above may be implemented with hardware components, software components, and/or combinations of hardware components and software components. For example, the apparatus and components described in the embodiments may be implemented with at least one general-purpose or special-purpose computer such as a processor, a controller, an arithmetic logic unit (ALU), a digital signal processor, a microcomputer, a field programmable gate array (FPGA), a programmable logic unit (PLU), a microprocessor, or any other device capable of executing and responding to instructions. The processing apparatus may execute an operating system (OS) and one or more software applications running on the operating system. The processing apparatus may also access, store, manipulate, process, and generate data in response to execution of software. For ease of understanding, although one processing apparatus is sometimes described as being used, one of ordinary skill in the art will understand that the processing apparatus may include a plurality of processing elements and/or a plurality of types of processing elements. For example, the processing apparatus may include a plurality of processors, or one processor and one controller. Other processing configurations are also possible, such as parallel processors.

The software may include a computer program, codes, instructions, or a combination of one or more thereof, and may configure the processing apparatus to operate as desired or may independently or collectively command the processing apparatus. The software and/or data may be permanently or temporarily embodied in any kind of machine, component, physical device, virtual equipment, computer storage medium or device, or transitory signal waves for being interpreted by the processing apparatus or for providing instructions or data to the processing apparatus. The software may be distributed over networked computer systems and stored or executed in a distributed manner. The software and data may be stored in one or more computer-readable recording media.

The methods of the embodiments may be implemented in the form of program instructions executable on various computer devices, and may be recorded in a computer-readable medium. The computer-readable medium may include program instructions, data files, data structures, and the like, alone or in combination. The program instructions recorded on the medium may be specially designed and configured for the embodiments, or may be known and available to those skilled in the art of computer software. Examples of the computer-readable recording medium include: magnetic media such as hard disks, floppy disks, and magnetic tapes; optical media such as CD-ROMs and DVDs; magneto-optical media such as floptical disks; and hardware devices such as ROMs, RAMs, and flash memories that are specially configured to store and execute program instructions. Examples of the program instructions include not only machine language codes such as those generated by compilers, but also high-level language codes that may be executed on computers using interpreters or the like. The hardware devices described above may each be configured to operate as one or more software modules to perform the operations of the embodiments, and vice versa.

Although the embodiments have been described with reference to limited examples and drawings, those skilled in the art may made various modifications and variations from the above descriptions thereof. For example, proper results may be achieved even though the above-described techniques are performed in an order different from those described above, and/or components of the above-described system, structure, apparatus, circuit, or the like are coupled or combined in a form different from those described above or are replaced or substituted with other components or equivalents.

Therefore, other implementations, other embodiments, and equivalents to the claims are also within the scope of the following claims.

The invention claimed is:

1. An apparatus for processing nuclear magnetic resonance and magnetic resonance spectroscopy data, the apparatus comprising:
a data storage unit configured to store training data, the training data including a plurality of pairs of incomplete data including at least one truncated section and ground truth data having no truncated section;
a data input unit configured to receive the training data from the data storage unit, receive input data from a magnetic resonator, and classify the input data into the ground truth data and the incomplete data;
a data recovery unit comprising a first artificial neural network training unit and a first artificial neural network prediction unit, wherein:
the first artificial neural network training unit is configured to receive the training data from the data input unit and train a first neural network to recover the incomplete data of the training data into the ground truth data of the training data, and
the first artificial neural network prediction unit is configured to receive the incomplete data of the input data from the data input unit, generate recovered data having no truncated section by recovering the truncated section from the incomplete data of the input data by using the first artificial neural network, and determine the input data as bad data when the incomplete data of the input data cannot be recovered;
a disease diagnosis unit comprising a second artificial neural network training unit and a second artificial neural network prediction unit, wherein:
the second artificial neural network training unit is configured to train a second artificial neural network based on at least one of the ground truth data received from the data input unit, the recovered data received from the data recovery unit, a signal obtained by fast Fourier transform (FFT) of the ground truth data, and a signal obtained by FFT of the recovered data to generate metabolite quantification data, and the second artificial neural network prediction unit is configured to determine a target metabolite that can distinguish between normal groups and patient groups for a specific disease using results obtained by categorizing and classifying the metabolite quantification data into sections according to a concentration range of a specific metabolite by using the second artificial neural network, and diagnose diseases based on concentration of the target metabolite; and a result output unit configured to output an error rate based on a true value for concentration of the target metabolite received from the second artificial neural network training unit and a predicted value for concentration of the target metabolite received from the second artificial neural network prediction unit, wherein the second artificial neural network prediction unit is configured to use a Moore-Penrose pseudoinverse matrix to calculate a multiplication coefficient value of each metabolite signal from the metabolite quantification data predicted by the second artificial neural network, the calculated multiplication coefficient value referring to an intrinsic concentration of each metabolite.

2. The apparatus of claim 1, wherein a noise signal includes any artifact element other than metabolites or baseline signals within the range of 0.5 ppm to 4.5 ppm in signal obtained by FFT of the input data, and wherein the data input unit is configured to classify the input data as the bad data depending on whether or not the artifact element is included and transmit the bad data and the incomplete data to the first artificial neural network prediction unit.

3. The apparatus of claim 1, wherein the first artificial neural network prediction unit is configured to divide the incomplete data by a designated unit and sequentially input the divided data to the first artificial neural network to obtain the recovered data.

4. The apparatus of claim 1, wherein the metabolite quantification data includes concentration data of the target metabolite, expressed the amount of the target metabolite as an absolute concentration or a relative concentration, wherein the second artificial neural network prediction unit is configured to:

obtain results of target metabolite detection based on whether the concentration data of the target metabolite exceeds a specified criterion by using the second artificial neural network, determine the target metabolite as detected if the concentration data of the target metabolite exceeds the specified criterion, generate disease diagnosis data based on the results of target metabolite detection, transmit the disease diagnosis data to the result output unit, and determine the presence of a disease corresponding to the target metabolite if the target metabolite is determined as detected.

5. The apparatus of claim 1, wherein the data input unit is configured to define the incomplete data from each of the input data and the training data by using at least one of a magnetic field strength, a data point value, and a frequency bandwidth included in a header of each of the input data and the training data, obtain a sampling time based on the data point value and define the incomplete data from the input data based on the sampling time.

6. The apparatus of claim 5, wherein the data input unit is configured to define the incomplete data from the input data, when the sampling time of the input data is shorter than a reference sampling time at a given magnetic field strength.

7. A method of processing nuclear magnetic resonance and magnetic resonance spectroscopy data by using a computing apparatus, the method comprising:

storing training data, the training data including a plurality of pairs of incomplete data including at least one truncated section and ground truth data having no truncated section;

receiving the training data and input data from a magnetic resonator;

classifying the input data into the ground truth data and the incomplete data;

training a first artificial neural network based on the training data to recover the incomplete data of the training data into the ground truth data of the training data;

generating recovered data having no truncated section by recovering the truncated section from the incomplete data of the input data by using the first artificial neural network;

determining the input data as bad data when the incomplete data of the input data cannot be recovered;

training a second artificial neural network based on at least one of the ground truth data, the recovered data, and a signal obtained by FFT of the ground truth data, and a signal obtained by FFT of the recovered data to generate metabolite quantification data;

determining a target metabolite that can distinguish between normal groups and patent groups for a specific disease using results obtained by categorizing and classifying the metabolite quantification data into sections according to a concentration range of a specific metabolite by using the second artificial neural network;

using a Moore-Penrose pseudoinverse matrix to calculate a multiplication coefficient value of each metabolite signal from the metabolite quantification data predicted by the second artificial neural network, the calculated multiplication coefficient value referring to an intrinsic concentration of each metabolite;

diagnosing diseases based on concentration of the target metabolite; and outputting an error rate based on a true value for concentration of the target metabolite and a predicted value for concentration of the target metabolite.

8. A non-transitory computer-readable medium having computer-readable instructions to cause a computer to perform the method of claim 7 using a computer.

* * * * *